(12) United States Patent
Samson et al.

(10) Patent No.: US 6,930,174 B2
(45) Date of Patent: Aug. 16, 2005

(54) CCR5 CHEMOKINE RECEPTOR-SPECIFIC ANTIBODIES

(75) Inventors: Michel Samson, Gentilly (FR); Marc Parmentier, Linkebeek (BE); Gilbert Vassart, Brussels (BE); Frederick Libert, Braine-l'Alleud (BE)

(73) Assignee: Euroscreen, s.a., Gosselies (BE)

( * ) Notice: Subject to any disclaimer, the term of this patent is extended or adjusted under 35 U.S.C. 154(b) by 211 days.

(21) Appl. No.: 09/938,703

(22) Filed: Aug. 24, 2001

(65) Prior Publication Data

US 2002/0110870 A1 Aug. 15, 2002

Related U.S. Application Data

(62) Division of application No. 09/626,939, filed on Jul. 27, 2000, now abandoned, which is a continuation of application No. 08/833,572, filed on Apr. 9, 1997, now Pat. No. 6,448,375, which is a continuation of application No. 08/810,028, filed on Mar. 4, 1997, now abandoned.

(30) Foreign Application Priority Data

| Mar. 1, 1996 | (EP) | 96870021 |
| Aug. 6, 1996 | (EP) | 96870102 |

(51) Int. Cl.[7] .......................... C07K 16/00; C07K 16/28
(52) U.S. Cl. .............. 530/387.9; 530/387.1; 530/387.9; 530/388.1; 530/388.15
(58) Field of Search .............. 530/351, 387.1, 530/387.7, 387.9, 388.1, 388.15; 435/9.1, 330, 331, 334

(56) References Cited

U.S. PATENT DOCUMENTS

| 5,928,881 A | 7/1999 | Barnette et al. | 435/7.21 |
| 6,025,154 A * | 2/2000 | Li et al. | 435/69.1 |
| 6,153,431 A * | 11/2000 | Beretta et al. | 435/372.3 |
| 6,265,184 B1 | 7/2001 | Gray et al. | 435/69.1 |
| 6,268,477 B1 | 7/2001 | Gray et al. | 530/350 |
| 6,511,826 B2 | 1/2003 | Li et al. | |

FOREIGN PATENT DOCUMENTS

| WO | WO 93/24134 | 12/1993 | |
| WO | WO 95/19436 | 7/1995 | |
| WO | WO 95/21245 | 8/1995 | |
| WO | WO 96/39437 | 12/1996 | |
| WO | 96/39437 | 12/1996 | C07K/14/705 |
| WO | WO 97/22698 | 6/1997 | |

OTHER PUBLICATIONS

Samson et al. (1996) *Molecular Cloning and Functional Expression of a New Human CC–Chemokine Receptor Gene*, Biochemistry 35:3362–3367.

Dragic et al. (Jun. 20, 1996) *HIV Entry into CD4+ cells is mediated by the chemokine receptor CC–CKR–5* Nature 381:667–73.

Deng et al. (Jun. 20, 1996) *Identification of a major co–receptor for primary isolates of HIV–1*, Nature 381:661–6.

International Search Report PCT BE 97/00023.

* cited by examiner

*Primary Examiner*—Brenda Brumback
(74) *Attorney, Agent, or Firm*—Palmer & Dodge LLP; Kathleen M. Williams

(57) ABSTRACT

A peptide has an amino acid sequence having more than 80% homology with the amino acid sequence listed as SEQ ID NO:4. A nucleic acid molecule has more than 80% homology with one of the nucleic acid sequences listed as SEQ ID NO:1, SEQ ID NO:2 and SEQ ID NO:3. Ligands, anti-ligands, cells vectors relating to the peptide and/or nucleic acid molecule are also used.

5 Claims, 20 Drawing Sheets

FIG. 1A

```
                                                              39 (UPPER: SEQ ID NO.: 1)
GAATTCCCCAACGAGAGCCAAGTCTCCATCTAGTGGACAGGGAAGCTAGCAGCAAACC   19 (LOWER: SEQ ID NO.: 4)

TTCCCTTCACTACAAACTTCATTGCTTGGCCAAAAGAGAGTTAATTCAATGTAGACAT   119
                                                              39

CTATGTAGGCAATTAAAACCTATTGATGTATAAAACAGTTTGCATTCATGGAGGCAAC   179
                                                              59

TAAATACATTCTAGGACTTTATAAAGATCACTTTTATTATGCACAGGGTGGAACAAG    239
                                                              79

ATGGATTATCAAGTGTCAAGTCCAATCTATGACATCAATTATTATACATGGAGCCCTGC  299
 M  D  Y  Q  V  S  S  P  I  Y  D  I  N  Y  Y  T  S  E  P  C   99
```

FIG. 1A-1

```
CAAAAAATCAATGTGAAGCAAATCGCAGCCCGCGCCTCCGCTCTACTCACTGGTG    359
 Q  K  I  N  V  K  Q  I  A  A  R  L  L  P  P  L  Y  S  L  V     119

TTCATCTTTGGTTTTGTGGGCAACATGCTGGTCATCCTCATCCTGATAAACTGCAAAAGG    419
 F  I  F  G  F  V  G  N  M  L  V  I  L  I  L  I  N  C  K  R     139

CTGAAGAGCATGACTGACATCTACCTGCTCAACCTGGCCATCTCTGACCTGTTTTTCCTT    479
 L  K  S  M  T  D  I  Y  L  L  N  L  A  I  S  D  L  F  F  L     159

CTTACTGTCCCCTTCTGGGCTCACTATGCTGCCGCAGTGGACTTTGGAAATACAATG       539
 L  T  V  P  F  W  A  H  Y  A  A  A  Q  W  D  F  G  N  T  M     179

TGTCAACTCTTGACAGGGCTCTATTTTATAGGCTTCTCTGGAATCTTCTTCATCATC      599
 C  Q  L  L  T  G  L  Y  F  I  G  F  S  G  I  F  F  I  I        199

CTCCTGACAATCGATAGGTACCTGGCTGTCGTCCATGCTGTTTGCTTTAAAGCCAGG      659
 L  L  T  I  D  R  Y  L  A  V  V  H  A  V  F  A  L  K  A  R     219

ACGGTCACCTTTGGGGTGGTGACAAGTGTGATCACTTGGGTGGTGGCTGTGTTGCGTCT    719
 T  V  T  F  G  V  V  T  S  V  I  T  W  V  V  A  V  F  A  S     239

CTCCCAGGAATCATCTTTACCAGATCTCAAAAGAAGTCTTCATTACACCTGCAGTCT      779
 L  P  G  I  I  F  T  R  S  Q  K  E  G  L  H  Y  T  C  S  S     259

CATTTCCATACA
 H  F  P  Y
```

GAATTCCCCCAACAGAGAGCCAAGCTCTCCATCTAGTGGACAGGGAAGCTAGCAGCAAACC    59 (UPPER: SEQ ID NO.: 2)
                                                                19 (LOWER: SEQ ID NO.: 5)

TTCCCTTCACTACAAAACTTCATTGCTTGGCCAAAAGAGAGTTAATTCAATGTAGACAT    119
                                                              39

CTATGTAGGCAATTAAAAACCTATTGATGTATAAAACAGTTTGCATTCATGGAGGGCAAC    179
                                                               59

TAAATACATTCTAGGACTTTATAAAGATCACTTTTTATTTATGCACAGGGTGGAACAAG    239
                                                              79

ATGGATTATCAAGTGTCAAGTCCAATCTATGACATCAATTATTATACATCGGAGCCCTGC    299
 M  D  Y  Q  V  S  S  P  I  Y  D  I  N  Y  Y  T  S  E  P  C    99

FIG. 1B-1

```
CAAAAAATCAATGTGAAGCAAATGCAGCCCGCCTCCGCTCTACTCACTGGTG   359
 Q  K  I  N  V  K  Q  I  A  A  R  L  L  P  P  L  Y  S  L  V    119

TTCATCTTTGGTTTTGTGGGCAACATGCTGGTCATCCTGATAAACTGCAAAAGG   419
 F  I  F  G  F  V  G  N  M  L  V  I  L  I  N  C  K  R    139

CTGAAGAGCATGACTGACATCTACCTGCTCAACCTGGCCATCTCTGACCTGTTTTTCCTT   479
 L  K  S  M  T  D  I  Y  L  L  N  L  A  I  S  D  L  F  F  L    159

CTTACTGTCCCCTTCTGGGCTCACTATGCGGCCGCCCAGTGGGACTTTGGAAATACAATG   539
 L  T  V  P  F  W  A  H  Y  A  A  A  Q  W  D  F  G  N  T  M    179

TGTCAACTCTTGACAGGCTCTATTTATAGGCTTCTCTGGAATCTTCTTCATCATC   599
 C  Q  L  L  T  G  L  Y  F  F  I  G  P  F  S  G  I  F  F  I  I    199

CTCCTGACAATCGATAGGTACCTGGCTGTCGTTGTCCATGCTGTGTTTGCTTTAAAGCCAGG   659
 L  L  T  I  D  R  Y  L  A  V  V  H  A  V  F  A  L  K  A  R    219

ACGGTCACCTTTGGGGTGGTGACAAGTGTGATCACTTGGGGTGTGGCTGTGTTTGCGTCT   719
 T  V  T  F  G  V  V  T  S  V  I  T  W  V  V  A  V  F  A  S    239

CTCCCAGGAATCATCTTTACCAGATCTCAAAAGAAGGTCTTCATTACCTGCAGCTCT   779
 L  P  G  I  I  F  T  R  S  Q  K  E  G  L  H  Y  T  C  S  S    259

CATTTTCCATACAGTCAGTATCAATTCTGGAAGAATTCCAGACATTAAAGATAGTCATC   839
 H  F  P  Y  S  Q  Y  Q  F  W  K  N  F  Q  T  L  K  I  V  I    279
```

FIG. 1B-2

```
TTGGGGCTGGTCCTGCCGCTTGTCATGTCATCTGTACTCGGAATCCTAAAAACT        899
 L  G  L  V  L  P  L  L  V  M  V  I  C  Y  S  G  I  L  K  T   299

CTGCTTCGGTGTGAAATGAGAGGCACAGAGGCTGTGAGGCTTATCTTCACCATC        959
 L  L  R  C  R  N  E  K  R  H  R  A  V  R  L  I  F  T  I     319

ATGATTGTTTATTTCTTCTTCTGGGCTCCCTACAACATGTCTTCTCTGAACACTTC     1019
 M  I  V  Y  F  L  F  W  A  P  Y  N  I  V  L  L  N  T  F     339

CAGGAATTCTTTGGCCTGAATAATTGCAGTAGCTCTAACAGGTTGGACCAAGCTATGCAG 1079
 Q  E  F  F  G  L  N  N  C  S  S  S  N  R  L  D  Q  A  M  Q  359

GTGACAGAGACTCTTGGGATGACGCACTGCTGCAACCCCATCATCAACCCCATCTATGCCTTGTC 1139
 V  T  E  T  L  G  M  T  H  C  C  I  N  P  I  I  Y  A  F  V  379

GGGGAGAAGTTCAGAAACTACCTCTTAGTCTTCTTCCAAAAGCACATTGCCAAACGCTTC 1199
 G  E  K  F  R  N  Y  L  L  V  F  F  Q  K  H  I  A  K  R  F  399

TGCAAATGCTGTCTATTTCCAGCAAGAGGCTCCCGAGCGAGCAAGCTCAGTTTACACC    1259
 C  K  C  C  S  I  F  Q  Q  E  A  P  E  R  A  S  S  V  Y  T  419

CGATCCACTGGGGAGCAGGAAATATCTGTGGGACTTGTGACACGGACTCAAGTGGGCTGGT 1319
 R  S  T  G  E  Q  E  I  S  V  G  L  *                        439

GACCCAGTCAGAGTTGTGCACACATGGCTTAGTTTTCATACACAGCCTGGGGGTNGG     1379
                                                              459

TTGGNNGAGGTCTTTTTTAAAGGAAGTTACTGTTATAGAGGTCTAAGATTCATCCATT    1439
                                                              479

TATTTGGCATCTGTGTTAAGTAGATTAGATCCGAATTC
```

```
GAATTCCCCCAACAGAGCCAAGCTCTCCATCTAGTGGACAGGAAGCTAGCAGCAAACC   59 (UPPER: SEQ ID NO. 3)
                                                             19 (LOWER: SEQ ID NO. 6)

TTCCCTTCACTACAAAACTTCATTGCTTGGCCAAAAGAGAGTTAATTCAATGTAGACAT  119
                                                             39

CTATGTAGGCAATTAAAAACCTATTGATGTATAAAACAGTTTGCATTCATGGAGGGCAAC 179
                                                             59

TAAATACATTCTAGGACTTTATAAAAGATCACTTTTTATTTATGCACAGGGTGGAACAAG 239
                                                             79

ATGGATTATCAAGTGTCAAGTCCAATCTATGACATCAATTATTATACATCGGAGCCCTGC 299
 M  D  Y  Q  V  S  S  P  I  Y  D  I  N  Y  Y  T  S  E  P  C   99
```

FIG. 1D-1

```
CAAAAAATCAATGTGAAGCAAATCGCAGCCCGAGCCCGCCTCCTACTCACTGGTG      359
 Q  K  I  N  V  K  Q  I  A  A  R  L  L  P  P  L  Y  S  L  V   119

TTCATCTTTGGTTTGTTGGGCAACATGCTGGTCATCCTGATAAACTGCAAAAGG        419
 F  I  F  G  F  V  G  N  M  L  V  I  L  I  N  C  K  R         139

CTGAAGAGCATGACTGACATTTACCTGCTCAACCTGGCCATCTCTGACCTGTTTTCTT    479
 L  K  S  M  T  D  I  Y  L  L  N  L  A  I  S  D  L  F  F  L   159

CTTACTGTCCCCTTCTGGGCTCACTATGCCGCCCAGTGGGACTTTGGAAATACAATG     539
 L  T  V  P  F  W  A  H  Y  A  A  A  Q  W  D  F  G  N  T  M   179

TGTCAACTCTTGACAGGGCTCTATTTTATAGGCTTCTTCTCTGGAATCTTCTTCATC     599
 C  Q  L  L  T  G  L  Y  F  I  G  F  F  S  G  I  F  F  I  I   199

CTCCTGACAATCGATAGGTACCTGGCCGTGGTCGTTCATGCGTGTTTTGCTTTAAAGCCAGG 659
 L  L  T  I  D  R  Y  L  A  V  V  H  A  V  F  A  L  K  A  R   219

ACGGTCACCTTTGGGGTGGTGACAAGTGTAATCACTTGGGTGGTGGCTGTTTTGCGTCT   719
 T  V  T  F  G  V  V  T  S  V  I  T  N  W  V  A  V  F  A  S   239

CTCCCAGGAATCATCTTTACGAGATCTCAAAAGAAGGTCTTCATTACACCTGCAGCTCT   779
 L  P  G  I  I  F  T  R  S  Q  K  E  G  L  H  Y  T  C  S  S   259

CATTTCCATACATTAAAGATAGTCATCTTGGGGCTGTCCGCTGCCGCTGCTTGTCATGT   839
 H  F  P  Y  I  K  D  S  H  L  G  A  G  P  A  A  A  C  H  G   279
```

FIG. 1D-2

```
CATCTGCTACTCGGAATCCTAAAAACTCGCTTCGGTGTCGAAATGAGAAGAGAGGCA        899
 H  L  L  G  N  P  K  N  S  A  S  V  S  K  *                    299
CAGGGCTGTGAGGCTTATCTTCACCATGATGTTTATTTCTCTCTGGCTCCCTA            959
                                                                 319
CAACATGTCCTTCTCCTGAACACCTTCCAGGAATTCTTTGGCCTGAATAATTGCAGTAG     1019
                                                                 339
CTCTAACAGGTTGGACCAAGCTATGCAGGTGACAGAGACTCTTGGGATGACGCACTGCTG    1079
                                                                 359
CATCAACCCCATCATCATGCCTTGTCGGGAGAAGTTCAGAAACTACCTCTTAGTCTT       1139
                                                                 379
CTTCCAAAAGCACATTGCCAAACGCTTCTGCAAATGCTGTCTATTTCCAGCAAGAGGC      1199
                                                                 399
TCCCGAGCGAGCAAGCTCAGTTTACACCCGATCCACTGGGGAGCAGGAAATATCTGTGGG    1259
                                                                 419
CTTGTGACACGGACTCAAGTGGGCTGGTGACCCAGTCAGAGTGTGCACATGGCTTAGTT     1319
                                                                 439
TTCATACACAGCCTGGGCTGGGGGTNGGTTGGNNGAGGTCTTTTTTAAAAGGAAGTTACT    1379
                                                                 459
GTTATAGAGGGTCTAAGATTCATCCATTTATTGGCATCTGTTTAAAGTAGATTAGATCC     1439
                                                                 479

GAATTC
```

|     |     | I | | II |
|---|---|---|---|---|
| CCR5 | 1 MDYQVSPIYDINYYTSEPCQKINVKQIAARLLPPLYSLVFIFGFVGNMLVILILINCKRLKSMTDIYLLNLAISDLFFLLT | | | 83 |
| hCC-R2b | 6 MLSTSRSRFIRNTNESGEEVTTFFDYDYGAPCHKFDVKQIGAQLLPPLYSLVFIFGFVGNMLVVLILINCKKLKCLTDIYLLNLAISDLLFLLT | | | 95 |
| hCC-R3 | MTTSLDTVETFGTTSYYDDVGLLCEKADTRALMAQFVPPLYSLVFTVGIIGNVVVVMILIKYRLKRLIMTNIYLLNLAISDLFLFLVT | | | 87 |
| hCC-R1 | METPNTTEDYDTTEFDYGDATPCQKVNERAFGAQLLPPLYSLVFVIGLVGNILVVLVLVQYKRLKNMTSIYLLNLAISDLLFLFT | | | 87 |
| hCC-R4 | MNPTDIADTTLDESIYSNYYLYESIPKPCTKEGIKAFGELFLPPLYSLVFVFGLLGNSVVVLVLFKYKRLRSMTDVYLLNLAISDLLFVFS | | | 92 |

|     | III | | IV | |
|---|---|---|---|---|
| CCR5 | VPFWAHYA..AAQWDFGNIMCQLLTGLYFIGFFSGIFFIILLTIDRYLAIVHAVFALKARTVTFGVTSVITWVAVFASLPGIIFTRSQKEGLH | | | 177 |
| hCC-R2b | LPLWAH..SAANEWVFGNAMCKLFTGLYHIGYFGGIFFIILLTIDRYLAIVHAVFALKARTVTFGVTSVITNLAVFASVPGIIFTKCQKEDSV | | | 189 |
| hCC-R3 | LPFWIHYVRGHNWVFGHGMCKLLSGFYHTGLYSEFFFIILLTIDRYLAIVHAVFALRARTVTFGVITSIVIWGLAVLAALPEFIFYETELFEE | | | 182 |
| hCC-R1 | LPFWIDYKLKDDWVFGDAMCKILSGFYYTGLYSEIFFIILLTIDRYLAIVHAVFALRARTVTFGVITSIIIWALAIASMPGLYFSKTQWEFTH | | | 182 |
| hCC-R4 | LPFWGYTA..ADQWVFGLGLCKMISWMLVGFVYSGIFFVMLMSIDRYLAIVHAVFSLRARTLTMGVIITSLATWSVAVFASLPGFLFSTCYTERNH | | | 186 |

FIG. 2

| FIG. 2A |
|---|
| FIG. 2B |

FIG. 2B

CCR5   F  P  Y  S  Q  Y  Q  F  W  K  N  F  Q  T  L  K  I  V  I  L  G  L  V  L  P
       TTTCCATATACAgtcagtatcaattctggaagaaTTAAAGATAGTCATCTTGGGGCTGGTCCTGCCG Δccr5  F  P  Y                                           I  K  D  S  H  L  G  A  G  P  A deletion CCR5   L  L  V  M  V  I  C  Y  S  G  I  L  K  T  L  L  R  C  R  N  E  K  K  R
       CTGCTTGTGTCATGGTCATCTGCTACTCGGGAATCCTAAAAACTCTGCTTCGGTGTCGAAATGAGAAGAAGAGG Δccr5  A  C  H  G  H  L  L  L  G  N  P  K  N  S  A  S  V  S  K  *

SEQUENCE LISTING

<160> NUMBER OF SEQ ID NOS: 18

<210> SEQ ID NO 1
<211> LENGTH: 792
<212> TYPE: DNA
<213> ORGANISM: Homo sapiens

<400> SEQUENCE: 1

| gaattccccc aacagagcca agctctccat ctagtggaca gggaagctag cagcaaacct | 60 |
| tcccttcact acaaaacttc attgcttggc caaaaagaga gttaattcaa tgtagacatc | 120 |
| tatgtaggca attaaaaacc tattgatgta taaaacagtt tgcattcatg gagggcaact | 180 |
| aaatacattc taggacttta taaaagatca ctttttattt atgcacaggg tggaacaaga | 240 |
| tggattatca agtgtcaagt ccaatctatg acatcaatta ttatacatcg gagccctgcc | 300 |
| aaaaaatcaa tgtgaagcaa atcgcagccc gcctcctgcc tccgctctac tcactggtgt | 360 |
| tcatctttgg ttttgtgggc aacatgctgg tcatcctcat cctgataaac tgcaaaaggc | 420 |
| tgaagagcat gactgacatc tacctgctca acctggccat ctctgacctg tttttccttc | 480 |
| ttactgtccc cttctgggct cactatgctg ccgcccagtg ggactttgga aatacaatgt | 540 |
| gtcaactctt gacagggctc tattttatag gcttcttctc tggaatcttc ttcatcatcc | 600 |
| tcctgacaat cgataggtac ctggctgtcg tccatgctgt gtttgcttta aaagccagga | 660 |
| cggtcacctt tggggtggtg acaagtgtga tcacttgggt ggtggctgtg tttgcgtctc | 720 |
| tcccaggaat catctttacc agatctcaaa agaaggtct tcattacacc tgcagctctc | 780 |
| attttccata ca | 792 |

<210> SEQ ID NO 2
<211> LENGTH: 1477
<212> TYPE: DNA
<213> ORGANISM: Homo sapiens
<220> FEATURE:
<221> NAME/KEY: misc_feature
<222> LOCATION: (1377)..(1377)
<223> OTHER INFORMATION: Any nucleotide
<220> FEATURE:
<221> NAME/KEY: misc_feature
<222> LOCATION: (1384)..(1385)
<223> OTHER INFORMATION: Any nucleotide

<400> SEQUENCE: 2

| gaattccccc aacagagcca agctctccat ctagtggaca gggaagctag cagcaaacct | 60 |
| tcccttcact acaaaacttc attgcttggc caaaaagaga gttaattcaa tgtagacatc | 120 |
| tatgtaggca attaaaaacc tattgatgta taaaacagtt tgcattcatg gagggcaact | 180 |
| aaatacattc taggacttta taaaagatca ctttttattt atgcacaggg tggaacaaga | 240 |
| tggattatca agtgtcaagt ccaatctatg acatcaatta ttatacatcg gagccctgcc | 300 |
| aaaaaatcaa tgtgaagcaa atcgcagccc gcctcctgcc tccgctctac tcactggtgt | 360 |
| tcatctttgg ttttgtgggc aacatgctgg tcatcctcat cctgataaac tgcaaaaggc | 420 |
| tgaagagcat gactgacatc tacctgctca acctggccat ctctgacctg tttttccttc | 480 |
| ttactgtccc cttctgggct cactatgctg ccgcccagtg ggactttgga aatacaatgt | 540 |
| gtcaactctt gacagggctc tattttatag gcttcttctc tggaatcttc ttcatcatcc | 600 |
| tcctgacaat cgataggtac ctggctgtcg tccatgctgt gtttgcttta aaagccagga | 660 |
| cggtcacctt tggggtggtg acaagtgtga tcacttgggt ggtggctgtg tttgcgtctc | 720 |

-continued

| | |
|---|---|
| tcccaggaat catctttacc agatctcaaa agaaggtct tcattacacc tgcagctctc | 780 |
| attttccata cagtcagtat caattctgga agaatttcca gacattaaag atagtcatct | 840 |
| tggggctggt cctgccgctg cttgtcatgg tcatctgcta ctcgggaatc ctaaaaactc | 900 |
| tgcttcggtg tcgaaatgag aagaagaggc acagggctgt gaggcttatc ttcaccatca | 960 |
| tgattgttta ttttctcttc tgggctccct acaacattgt ccttctcctg aacaccttcc | 1020 |
| aggaattctt tggcctgaat aattgcagta gctctaacag gttggaccaa gctatgcagg | 1080 |
| tgacagagac tcttgggatg acgcactgct gcatcaaccc catcatctat gcctttgtcg | 1140 |
| gggagaagtt cagaaactac ctcttagtct tcttccaaaa gcacattgcc aaacgcttct | 1200 |
| gcaaatgctg ttctattttc cagcaagagg ctcccgagcg agcaagctca gtttacaccc | 1260 |
| gatccactgg ggagcaggaa atatctgtgg gcttgtgaca cggactcaag tgggctggtg | 1320 |
| acccagtcag agttgtgcac atggcttagt tttcatacac agcctgggct gggggtnggt | 1380 |
| tggnngaggt cttttttaaa aggaagttac tgttatagag ggtctaagat tcatccattt | 1440 |
| atttggcatc tgtttaaagt agattagatc cgaattc | 1477 |

<210> SEQ ID NO 3
<211> LENGTH: 1442
<212> TYPE: DNA
<213> ORGANISM: Homo sapiens

<400> SEQUENCE: 3

| | |
|---|---|
| gaattccccc aacagagcca agctctccat ctagtggaca gggaagctag cagcaaacct | 60 |
| tcccttcact acaaaacttc attgcttggc caaaagaga gttaattcaa tgtagacatc | 120 |
| tatgtaggca attaaaaacc tattgatgta taaaacagtt tgcattcatg gagggcaact | 180 |
| aaatacattc taggacttta taaaagatca cttttatttt atgcacaggg tggaacaaga | 240 |
| tggattatca agtgtcaagt ccaatctatg acatcaatta ttatacatcg gagccctgcc | 300 |
| aaaaaatcaa tgtgaagcaa atcgcagccc gcctcctgcc tccgctctac tcactggtgt | 360 |
| tcatctttgg ttttgtgggc aacatgctgg tcatcctcat cctgataaac tgcaaaaggc | 420 |
| tgaagagcat gactgacatc tacctgctca acctggccat ctctgacctg ttttccttc | 480 |
| ttactgtccc cttctgggct cactatgctg ccgcccagtg ggactttgga aatacaatgt | 540 |
| gtcaactctt gacagggctc tattttatag gcttcttctc tggaatcttc ttcatcatcc | 600 |
| tcctgacaat cgataggtac ctggctgtcg tccatgctgt gtttgcttta aaagccagga | 660 |
| cggtcacctt tggggtggtg acaagtgtga tcacttgggt ggtggctgtg tttgcgtctc | 720 |
| tcccaggaat catctttacc agatctcaaa agaaggtct tcattacacc tgcagctctc | 780 |
| attttccata cattaaagat agtcatcttg gggctggtcc tgccgctgct tgtcatggtc | 840 |
| atctgctact cgggaatcct aaaaactctg cttcggtgtc gaaatgagaa gaagaggcac | 900 |
| agggctgtga ggcttatctt caccatcatg attgtttatt ttctcttctg ggctccctac | 960 |
| aacattgtcc ttctcctgaa caccttccag gaattctttg gcctgaataa ttgcagtagc | 1020 |
| tctaacaggt tggaccaagc tatgcaggtg acagagactc ttgggatgac gcactgctgc | 1080 |
| atcaaccccc tcatctatgc ctttgtcggg agaagttca gaaactacct cttagtcttc | 1140 |
| ttccaaaagc acattgccaa acgcttctgc aaatgctgtt ctattttcca gcaagaggct | 1200 |
| cccgagcgag caagctcagt ttacacccga tccactgggg agcaggaaat atctgtgggc | 1260 |
| ttgtgacacg gactcaagtg ggctggtgac ccagtcagag ttgtgcacat ggcttagttt | 1320 |

```
tcatacacag cctgggctgg gggtggttgg gaggtctttt ttaaaaggaa gttactgtta    1380
tagagggtct aagattcatc catttatttg gcatctgttt aaagtagatt agatccgaat    1440
tc                                                                  1442
```

<210> SEQ ID NO 4
<211> LENGTH: 184
<212> TYPE: PRT
<213> ORGANISM: Homo sapiens

<400> SEQUENCE: 4

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr
            180
```

<210> SEQ ID NO 5
<211> LENGTH: 352
<212> TYPE: PRT
<213> ORGANISM: Homo sapiens

<400> SEQUENCE: 5

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110
```

```
Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 6
<211> LENGTH: 215
<212> TYPE: PRT
<213> ORGANISM: Homo sapiens

<400> SEQUENCE: 6

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140
```

```
Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
            165                 170                 175

Thr Cys Ser Ser His Phe Pro Tyr Ile Lys Asp Ser His Leu Gly Ala
            180                 185                 190

Gly Pro Ala Ala Ala Cys His Gly His Leu Leu Leu Gly Asn Pro Lys
            195                 200                 205

Asn Ser Ala Ser Val Ser Lys
    210                 215

<210> SEQ ID NO 7
<211> LENGTH: 360
<212> TYPE: PRT
<213> ORGANISM: Homo sapiens
<220> FEATURE:
<221> NAME/KEY: MISC_FEATURE
<222> LOCATION: (325)..(327)
<223> OTHER INFORMATION: Xaa = any amino acid

<400> SEQUENCE: 7

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Ile Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
            165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
    195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270
```

```
Gly Leu Ser Asn Cys Glu Ser Thr Ser Gln Leu Asp Gln Ala Ile Gln
            275                 280                 285

Val Thr Glu Thr Leu Gly Met Thr His Cys Cys Ile Asn Pro Ile Ile
        290                 295                 300

Tyr Ala Phe Val Gly Glu Lys Phe Arg Arg Tyr Ile Ser Val Phe Phe
305                 310                 315                 320

Arg Lys His Ile Xaa Xaa Xaa Phe Cys Lys Gln Cys Pro Val Phe Tyr
                    325                 330                 335

Arg Glu Thr Val Asp Gly Val Thr Ser Thr Asn Thr Pro Ser Thr Gly
            340                 345                 350

Glu Gln Glu Val Ser Ala Gly Leu
            355                 360

<210> SEQ ID NO 8
<211> LENGTH: 355
<212> TYPE: PRT
<213> ORGANISM: Homo sapiens
<220> FEATURE:
<221> NAME/KEY: MISC_FEATURE
<222> LOCATION: (231)..(233)
<223> OTHER INFORMATION: Xaa = amy amino acid
<220> FEATURE:
<221> NAME/KEY: MISC_FEATURE
<222> LOCATION: (333)..(335)
<223> OTHER INFORMATION: Xaa = amy amino acid

<400> SEQUENCE: 8

Met Thr Thr Ser Ile Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Val Pro Pro Leu Tyr Ser Leu Val Phe Thr Val Gly
            35                  40                  45

Leu Ile Gly Asn Val Val Val Val Met Ile Leu Ile Lys Tyr Arg Arg
    50                  55                  60

Ile Arg Ile Met Thr Asn Ile Tyr Leu Leu Asn Leu Ala Ile Ser Asp
65                  70                  75                  80

Leu Leu Phe Ile Val Thr Leu Pro Phe Trp Thr His Tyr Val Arg Gly
                85                  90                  95

His Asn Trp Val Phe Gly His Gly Met Cys Asn Leu Ile Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Ile Arg Ala
    130                 135                 140

Arg Thr Val Thr Phe Gly Val Ile Thr Ser Ile Val Thr Trp Gly Ile
145                 150                 155                 160

Ala Val Ile Ala Ala Leu Pro Glu Phe Ile Phe Tyr Glu Thr Glu Glu
                165                 170                 175

Leu Phe Glu Glu Thr Ile Cys Ser Ala Leu Tyr Pro Glu Asp Thr Val
            180                 185                 190

Tyr Ser Trp Arg His Phe His Thr Ile Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Xaa Xaa Xaa Lys Tyr Lys Ala Ile Arg Leu
225                 230                 235                 240
```

```
Ile Phe Val Ile Met Ala Val Phe Phe Ile Glu Trp Thr Pro Tyr Asn
                245                 250                 255

Val Ala Ile Leu Ile Ser Ser Tyr Gln Ser Leu Leu Phe Gly Asn Asn
            260                 265                 270

Cys Glu Arg Ser Lys His Leu Asp Leu Val Met Ile Val Thr Glu Val
            275                 280                 285

Ile Ala Tyr Ser His Cys Cys Met Asn Glu Val Ile Tyr Ala Phe Val
        290                 295                 300

Gly Glu Arg Phe Arg Lys Tyr Ile Arg His Phe His Arg His Leu
305                 310                 315                 320

Leu Met His Leu Gly Arg Tyr Ile Pro Phe Leu Pro Xaa Xaa Xaa Ile
                325                 330                 335

Glu Arg Ile Ser Ser Val Ser Pro Ser Thr Ala Glu Pro Glu Ile Ser
                340                 345                 350

Ile Val Phe
        355

<210> SEQ ID NO 9
<211> LENGTH: 355
<212> TYPE: PRT
<213> ORGANISM: Homo sapiens

<400> SEQUENCE: 9

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Ile Phe Thr Leu Pro Phe Trp Ile Asp Tyr Lys Leu Lys
                85                  90                  95

Asp Asp Trp Val Phe Gly Asp Ala Met Cys Lys Ile Ile Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Ile Arg Ala
    130                 135                 140

Arg Thr Val Thr Phe Gly Val Ile Thr Ser Ile Ile Ile Trp Ala Ile
145                 150                 155                 160

Ala Ile Ile Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Ile Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Ile Pro Tyr Asn
                245                 250                 255
```

-continued

```
Leu Thr Ile Ile Ile Ser Val Phe Gln Asp Phe Leu Phe Thr His Glu
            260                 265                 270

Cys Glu Gln Ser Arg His Leu Asp Leu Ala Val Gln Val Thr Glu Val
            275                 280                 285

Ile Ala Tyr Thr His Cys Cys Val Asn Glu Val Ile Tyr Ala Phe Val
            290                 295                 300

Gly Glu Arg Phe Arg Lys Tyr Ile Arg Gln Leu Glu His Arg Val
305                 310                 315                 320

Ala Val His Leu Val Lys Trp Leu Pro Phe Leu Ser Val Asp Arg Ile
            325                 330                 335

Glu Arg Val Ser Ser Thr Ser Pro Ser Thr Gly Glu His Glu Ile Ser
            340                 345                 350

Ala Gly Phe
        355

<210> SEQ ID NO 10
<211> LENGTH: 360
<212> TYPE: PRT
<213> ORGANISM: Homo sapiens
<220> FEATURE:
<221> NAME/KEY: MISC_FEATURE
<222> LOCATION: (145)..(147)
<223> OTHER INFORMATION: Xaa = any amino acid
<220> FEATURE:
<221> NAME/KEY: MISC_FEATURE
<222> LOCATION: (321)..(323)
<223> OTHER INFORMATION: Xaa = any amino acid

<400> SEQUENCE: 10

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
            35                  40                  45

Val Glu Val Phe Gly Leu Ile Gly Asn Ser Val Val Leu Val Leu
            50                  55                  60

Phe Lys Tyr Lys Arg Ile Arg Ser Met Thr Asp Val Tyr Leu Leu Asn
65                  70                  75                  80

Leu Ala Ile Ser Asp Leu Leu Phe Val Phe Ser Leu Pro Phe Trp Gly
            85                  90                  95

Tyr Tyr Ala Ala Asp Gln Trp Val Phe Gly Leu Gly Ile Cys Lys Met
            100                 105                 110

Ile Ser Trp Met Tyr Leu Val Gly Phe Tyr Ser Gly Ile Phe Phe Val
            115                 120                 125

Met Ile Met Ser Ile Asp Arg Tyr Leu Ala Ile Val His Ala Val Glu
130                 135                 140

Xaa Xaa Xaa Ala Arg Thr Ile Ile Tyr Gly Val Ile Thr Ser Leu Ala
145                 150                 155                 160

Thr Trp Ser Val Ala Val Phe Ala Ser Leu Pro Gly Phe Ile Phe Ser
            165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
            210                 215                 220
```

```
Ile Ile Arg Thr Leu Gln His Cys Lys Asn Glu Lys Asn Lys Ala
225                 230                 235                 240

Val Lys Met Ile Phe Ala Val Val Leu Phe Leu Gly Phe Trp Thr
            245                 250                 255

Pro Tyr Asn Ile Val Leu Phe Leu Glu Thr Leu Val Glu Leu Val
            260                 265                 270

Ile Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Ile Gln Leu Phe Lys
305                 310                 315                 320

Xaa Xaa Xaa Gly Leu Phe Val Ile Cys Gln Tyr Cys Gly Leu Leu Gln
                325                 330                 335

Ile Tyr Ser Ala Asp Thr Pro Ser Ser Ser Tyr Thr Gln Ser Thr Met
        340                 345                 350

Asp His Asp Leu His Asp Ala Leu
        355                 360

<210> SEQ ID NO 11
<211> LENGTH: 49
<212> TYPE: PRT
<213> ORGANISM: Homo sapiens

<400> SEQUENCE: 11

Phe Pro Tyr Ser Gln Tyr Gln Phe Trp Lys Asn Phe Gln Thr Leu Lys
1               5                   10                  15

Ile Val Ile Leu Gly Leu Val Leu Pro Leu Leu Val Met Val Ile Cys
            20                  25                  30

Tyr Ser Gly Ile Leu Lys Thr Leu Leu Arg Cys Arg Asn Glu Lys Lys
        35                  40                  45

Arg

<210> SEQ ID NO 12
<211> LENGTH: 147
<212> TYPE: DNA
<213> ORGANISM: Homo sapiens

<400> SEQUENCE: 12
tttccataca gtcagtatca attctggaag aatttccaga cattaaagat agtcatcttg     60
gggctggtcc tgccgctgct tgtcatggtc atctgctact cgggaatcct aaaaactctg    120
cttcggtgtc gaaatgagaa gaagagg                                        147

<210> SEQ ID NO 13
<211> LENGTH: 34
<212> TYPE: PRT
<213> ORGANISM: Homo sapiens

<400> SEQUENCE: 13

Phe Pro Tyr Ile Lys Asp Ser His Leu Gly Ala Gly Pro Ala Ala Ala
1               5                   10                  15

Cys His Gly His Leu Leu Leu Gly Asn Pro Lys Asn Ser Ala Ser Val
            20                  25                  30

Ser Lys

<210> SEQ ID NO 14
```

-continued

```
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: Primer used to amplify the full size coding
      region of the CCR5 gene

<400> SEQUENCE: 14
tcgaggatcc aagatggatt atcaagt                                          27

<210> SEQ ID NO 15
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: Primer to amplify the full size coding
      region of the CCR5 gene

<400> SEQUENCE: 15
ctgatctaga gccatgtgca caactct                                          27

<210> SEQ ID NO 16
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: Primer used to amplify CCR5 from genomic DNA
      samples

<400> SEQUENCE: 16
cctggctgtc gtccatgctg                                                  20

<210> SEQ ID NO 17
<211> LENGTH: 27
<212> TYPE: DNA
<213> ORGANISM: Artificial Sequence
<220> FEATURE:
<221> NAME/KEY: primer_bind
<222> LOCATION: (1)..(27)
<223> OTHER INFORMATION: primer used to amplify  CCR5 from genomic DNA
      samples

<400> SEQUENCE: 17
ctgatctaga gccatgtgca caactct                                          27

<210> SEQ ID NO 18
<211> LENGTH: 215
<212> TYPE: PRT
<213> ORGANISM: Homo sapiens

<400> SEQUENCE: 18

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60
```

-continued

```
Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
            85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
            165                 170                 175

Thr Cys Ser Ser His Phe Pro Tyr Ile Lys Asp Ser His Leu Gly Ala
            180                 185                 190

Gly Pro Ala Ala Ala Cys His Gly His Leu Leu Leu Gly Asn Pro Lys
        195                 200                 205

Asn Ser Ala Ser Val Ser Lys
        210                 215
```

CCR5 CHEMOKINE RECEPTOR-SPECIFIC ANTIBODIES

This application is a divisional of U.S. patent application Ser. No. 09/626,939, filed Jul. 27, 2000, now abandoned, which is a continuation of U.S. patent application Ser. No. 08/833,752, filed Apr. 9, 1997, now U.S. Pat. No. 6,448,375, which is a continuation of U.S. patent application Ser. No. 08/810,028, filed Mar. 4, 1997, now abandoned, which claims priority under 35 U.S.C. § 119(a)–(d) to EP 96870021.1, filed Mar. 1, 1996, and EP 96870102.9, filed Aug. 6, 1996.

BACKGROUND

1. Field of the Invention

The present invention concerns new peptides and the nucleic acid molecules encoding said peptides, the vector comprising said nucleic acid molecules, the cells transformed by said vector, inhibitors directed against said peptides or said nucleic acid molecules, a pharmaceutical composition and a diagnostic and/or dosage device comprising said products, and non human transgenic animals expressing the peptides according to the invention or the nucleic acid molecules encoding said peptides.

The invention further provides a method for determining ligand binding, detecting expression, screening for drugs binding specifically to said peptides and treatments involving the peptides or the nucleic acid molecules according to the invention.

2. Technological Background of the Art

Chemotactic cytokines, or chemokines, are small signalling proteins that can be divided in two subfamilies (CC- and CXC-chemokines) depending on the relative position of the first two conserved cysteines. Interleukin 8 (IL-8) is the most studied of these proteins, but a large number of chemokines (Regulated on Activation Normal T-cell Expressed and Secreted (RANTES), Monocyte Chemoattractant Protein 1 (MCP-1), Monocyte Chemoattractant Protein 2 (MCP-2), Monocyte Chemoattractant Protein 3 (MCP-3), Growth-Related gene product a (GROα), Growth-Related gene product β (GRO)β, Growth-Related gene product γ (GROγ), Macrophage Inflammatory Protein 1 α (MIP-1α) and β, etc.) has now been described [4]. Chemokines play fundamental roles in the physiology of acute and chronic inflammatory processes as well as in the pathological dysregulations of these processes, by attracting and simulating specific subsets of leucocytes [32]. RANTES for example is a chemoattractant for monocytes, memory T-cells and eosinophils, and induces the release of histamine by basophils. MCP-1, released by smooth muscle cells in arteriosclerotic lesions, is considered as the factor (or one of the factors) responsible for macrophage attraction and, therefore, for the progressive aggravation of the lesions [4].

MIP-1α, MIP-1β and RANTES chemokines have recently been described as major HIV-1 suppressive factors produced by CD8[+] T-cells [9]. CC-chemokines are also involved in the regulation of human myeloid progenetor cell proliferation [6, 7].

Recent studies have demonstrated that the actions of CC- and CXC-chemokines are mediated by subfamilies of G protein-coupled receptors. To date, despite the numerous functions attributed to chemokines and the increasing number of biologically active ligands, only six functional receptors have been identified in human. Two receptors for interleukin-8 (IL-8) have been described [20, 29]. One (IL-8RA) binds IL-8 specifically, while the other (IL-8RB) binds IL-8 and other CXC-chemokines, like GRO. Among receptors binding CC-chemokines, a receptor, designated CC-chemokine receptor 1 (CCR1), binds both RANTES and MIP-1α [31], and the CC-chemokine receptor 2 (CCR2) binds MCP-1 and MCP-3 [8, 44, 15]. Two additional CC-chemokine receptors were cloned recently: the CC-chemokine receptor 3 (CCR3) was found to be activated by RANTES, MIP-1α and MIP-1β [10]; the CC-chemokine receptor 4 (CCR4) responds to MIP-1, RANTES and MCP-1 [37]. In addition to these six functional receptors, a number of orphan receptors have been cloned from human and other species, that are structurally related to either CC- or CXC-chemokine receptors. These include the human BLR1 [13], EBI1 [5], LCR1 [21], the mouse MIP-1 RL1 and MIP-1 RL2 [17] and the bovine PPR1 [25]. Their respective ligand(s) and function(s) are unknown at present.

SUMMARY OF THE INVENTION

The present invention is related to a peptide having at least an amino acid sequence which presents more than 80%, advantageously more than 90%, preferably more than 95%, homology with the amino acid sequence as represented in SEQ ID NO. 1.

Preferably, said peptide has also at least an amino acid sequence which presents more than 80%, advantageously more than 90%, preferably more than 95%, homology with the amino acid sequence as represented in SEQ ID NO. 2.

According to another embodiment of the present invention, the peptide has at least an amino acid sequence which presents more than 80%, advantageously more than 90%, preferably more than 95%, homology with the amino acid sequence as represented in SEQ ID NO. 3.

The present invention is also related to the amino acid sequence of SEQ ID NO. 1, SEQ ID NO. 2, SEQ ID NO. 3 or a portion thereof (represented in the FIG. 1).

A "portion of an amino acid sequence" means one or more amino acid segments having the same or improved binding properties of the whole peptide according to the invention. Said portion could be an epitope which is specifically binded by a ligand of the peptide which could be a known "natural ligand" of said peptide, an agonist or an analog of said ligand, or an inhibitor capable of competitively inhibiting the binding of said ligand to the peptide (including the antagonists of said ligand to the peptide).

Specific examples of said portions of amino acid sequence and their preparation process are described in the publication of Rucker J. et al. (Cell, Vol. 87, pp. 437–446 (1996)) incorporated herein by reference.

According to the invention, said portion of the amino acid sequence of the peptide according to the invention comprises the N-terminus segment and the first extracellular loop of the peptide.

Therefore, according to the invention, the amino acid sequence as represented in SEQ ID NO. 1 is the common amino acid sequence of SEQ ID NO. 2 and of SEQ ID NO. 3 (see also FIG. 1). Therefore, a first industrial application of said amino acid sequence is the identification of the homology between said amino acid sequence and the screening of various mutants encoding a different amino acid sequence than the one previously described, and the identification of various types of patient which may present a predisposition or a resistance to the disorders described in the following specification.

Preferably, the peptide according to the invention or a portion thereof is an active CC-chemokine receptor.

Advantageously, the CC-chemokine receptor according to the invention is stimulated by the MIP-1β chemokine at a concentration less or equal to 10 nm, and is advantageously also stimulated by the MIP-1α or RANTES chemokines. However, said chemokine receptor is not stimulated by the MCP-1, MCP-2, MCP-3, IL-8 and GROα chemokines.

In addition, the peptide according to the invention or a portion thereof is also a receptor of HIV viruses or a portion of said HIV viruses.

It is meant by "HIV viruses", HIV-1 or HIV-2 and all the various strains of HIV viruses which are involved in the development of AIDS. It is meant by a "a portion of HIV viruses", any epitope of said viruses which is able to interact specifically with said receptor. Among said portions of viruses which may be involved in the interaction with the peptide according to the invention, are peptides encoded by the ENV and GAG viruses genes.

Preferably, said portion of HTV viruses is the glycopeptide gp120/160 (membrane-bound gp160 or the free gp derived therefrom) or a portion thereof.

It is meant by a "portion of the glycopeptide gp120/160" any epitope, preferably an immuno-dominant epitope, of said glycopeptide which may interact specifically with the peptide according to the invention, such as for instance the V3 loop (third hypervariable domain).

According to another embodiment of the present invention, the peptide according to the invention is an inactive CC-chemokine receptor. An example of such inactive CC-chemokine receptor is encoded by the amino acid sequence as represented in SEQ ID NO. 2.

It is meant by an "inactive CC-chemokine receptor" a receptor which is not stimulated by any known CC-chemokine, especially the MIP-1α, MIP-1α or RANTES chemokines.

The peptide represented in SEQ ID NO. 3 according to the invention is an 30 inactive receptor which is not a receptor of HIV viruses or of a portion of said HIV viruses, which means that said inactive receptor does not allow the entry of said FHV viruses into a cell which presents at its surface said inactive receptor.

Advantageously, the peptide according to the invention is a human receptor.

The present invention concerns also the nucleic acid molecule having more than 80%, preferably more than 90%, homology with one of the nucleic acid sequences of SEQ ID NO. 1, SEQ ID NO. 2 and SEQ ID NO. 3 shown in the FIG. 1.

Preferably, said nucleic acid molecule has at least the nucleic acid sequence shown in SEQ ID NO. 1, SEQ ID NO. 2 or SEQ ID NO. 3 of FIG. 1 or a portion thereof.

It is meant by a "portion of said nucleic acid molecule" any nucleic acid sequence of more than 15 nucleotides which could be used in order to detect and/or reconstitute said nucleic acid molecule or its complementary strand. Such portion could be a probe or a primer which could be used in genetic amplification using the PCR, LCR, NASBA or CPR techniques for instance.

The present invention concerns more specifically the nucleic acid molecules encoding the peptide according to the invention. Said nucleic acid molecules are RNA or DNA molecules such as a cDNA molecule or a genomic DNA molecule.

The present invention is also related to a vector comprising the nucleic acid molecule according to the invention. Preferably, said vector is adapted for expression in a cell and comprises the regulatory elements necessary for expressing the amino acid molecule in said cell operatively linked to the nucleic acid sequence according to the invention as to permit expression thereof.

Preferably, said cell is chosen among the group consisting of bacterial cells, yeast cells, insect cells or mammalian cells. The vector according to the invention is a plasmid, preferably a pcDNA3 plasmid, or a virus, preferably a baculovirus, an adenovirus or a semliki forest virus.

The present invention concerns also the cell, preferably a mammalian cell, such as a CHO-K1 or a HEK293 cell, transformed by the vector according to the invention. Advantageously, said cell is non neuronal in origin and is chosen among the group consisting of CHO-K1, HEK293, BHK21, COS-7 cells.

The present invention also concerns the cell (preferably a mammalian cell such as a CHO-K1 cell) transformed by the vector according to the invention and by another vector encoding a protein enhancing the functional response in said cell. Advantageously, said protein is the Gα15 or Gα16 (G protein, α subunit). Advantageously, said cellis the cell CHO-K1-pEFIN hCCR5-1/16.

The present invention is also related to a nucleic acid probe comprising a nucleic acid molecule of at least 15 nucleotides capable of specifically hybridizing with a unique sequence included within the sequence of the nucleic acid molecule according to the invention. Said nucleic acid probe may be a DNA or a RNA.

The invention concerns also an antisense oligonucleotide having a sequence capable of specifically hybridizing to an MRNA molecule encoding the peptide according to the invention so as to prevent translation of said MIRNA molecule or an antisense oligonucleotide having a sequence capable of specifically hybridizing to the CDNA molecule encoding the peptide according to the invention.

Said antisense oligonucleotide may comprise chemical analogs of nucleotide or substances which inactivate MRNA, or be included in an RNA molecule endowed with ribozyme activity.

Another aspect of the present invention concerns a ligand or an anti-ligand (preferably an antibody) other than known "natural ligands", which are chosen among the group consisting of the MIP-1β, MIP-1α or RANTES chemokines, HIV viruses or a portion of said HI viruses, wherein said ligand is capable of binding to the receptor according to the invention and wherein said anti-ligand is capable of (preferably competitively) inhibiting the binding of said known "natural ligand" or the ligand according to the invention to the peptide according to the invention.

The exclusion in the above identified definition of known chemokines, HIV viruses or a portion of said HIV viruses, does not include variants of said "natural" viruses or said "natural" portion which may be obtained for instance by genetic engineering and which may mimic the interaction of said viruses and portion of said viruses to the peptide according to the invention.

Advantageously, said antibody is a monoclonal antibody which is preferably directed to an epitope of the peptide according to the invention and present on the surface of a cell expressing said peptide. One embodiment of the instant invention is an antibody which binds to a polypeptide encoded by a nucleic acid comprising residues 792 to 884 of SEQ ID NO: 3, wherein said nolvnentide has the same reading frame as the sequence of SEQ ID NO: 6.

Preferably, said antibody is produced by the hybridome cell AchCCR5-SAB1A7.

The invention concerns also the pharmaceutical composition comprising either an effective amount of the peptide according to the invention (in order to delude the HIV virus from the natural peptide present at the surface of a mammalian cell and stop the infection of said mammalian cell by the HIV virus), or an effective amount of the above identified described ligand and/or anti-ligand, or an effective amount of oligonucleotide according to the invention, effective to decrease the activity of said peptide by passing through a cell membrane and binding specifically with MRNA encoding the peptide according to the invention in the cell so as to prevent it translation. The pharmaceutical composition comprises also a pharmaceutically acceptable carrier, preferably capable of passing through said cell membrane.

Preferably, in said pharmaceutical composition, the oligonucleotide is coupled to a substance, such as a ribozyme, which inactivates MRNA encoding the peptide according to the invention.

Preferably, the pharmaceutically acceptable carrier comprises a structure which binds to a receptor on a cell capable of being taken up by cell after binding to the structure. The structure of the pharmaceutically acceptable carrier in said pharmaceutical composition is capable of binding to a receptor which is specific for a selected cell type.

The present invention concerns also a transgenic non human mammal overexpressing (or expressing ectopically) the nucleic acid molecule encoding the peptide according to the invention.

The present invention also concerns a transgenic non human mammal comprising an homologous recombination knockout of the native peptide according to the invention.

According to a preferred embodiment of the invention, the transgenic non human mammal whose genome comprises antisense nucleic acid complementary to the nucleic acid according to the invention is so placed as to be transcripted into antisense MRNA which is complementary to the MRNA encoding the peptide according to the invention and which hybridizes to MRNA encoding said peptide, thereby reducing its translation. Preferably, the transgenic non human mammal according to the invention comprises a nucleic acid molecule encoding the peptide according to the invention and comprises additionally an inducible promoter or a tissue specific regulatory element.

Preferably, the transgenic non human mammal is a mouse.

The invention relates to a method for determining whether a ligand can be specifically bound to the peptide according to the invention, which comprises contacting a cell transfected with a vector expressing the nucleic acid molecule encoding said peptide with the ligand under conditions permitting binding of ligand to such peptide and detecting the presence of any such ligand bound specifically to said peptide, thereby determining whether the ligand binds specifically to said peptide.

The invention relates to a method for determining whether a ligand can specifically bind to a peptide according to the invention, which comprises preparing a cell extract from cells transfected with a vector expressing the nucleic acid molecule encoding said peptide, isolating a membrane fraction from the cell extract, contacting the ligand with the membrane fraction under conditions permitting binding of the ligand to such peptide and detecting the presence of any ligand bound to said peptide, thereby determining whether the compound is capable of specifically binding to said peptide. Preferably, said method is used when the ligand is not previously known.

The invention relates to a method for determining whether a ligand is an agonist of the peptide according to the invention, which comprises contacting a cell transfected with a vector expressing the nucleic acid molecule encoding said peptide with the ligand under conditions permitting the activation of a functional peptide response from the cell and detecting by means of a bio-assay, such as a modification in a second messenger concentration (preferably calcium ions or inositol phosphates such as $IP_3$) or a modification in the cellular metabolism (preferably determined by the acidification rate of the culture medium), an increase in the peptide activity, thereby determining whether the ligand is a peptide agonist.

The invention relates to a method for determining whether a ligand is an agonist of the peptide according to the invention, which comprises preparing a cell extract from cells transfected with a vector expressing the nucleic acid molecule encoding said peptide, isolating a membrane fraction from the cell extract, contacting the membrane fraction with the ligand under conditions permitting the activation of a functional peptide response and detecting by means of a bio-assay, such as a modification in the production of a second messenger (preferably inositol phosphates such as $IP_3$), an increase in the peptide activity, thereby determining whether the ligand is a peptide agonist.

The present invention relates to a method for determining whether a ligand is an antagonist of the peptide according to the invention, which comprises contacting a cell transfected with a vector expressing the nucleic acid molecule encoding said peptide with the ligand in the presence of a known peptide agonist, under conditions permitting the activation of a functional peptide response and detecting by means of a bio-assay, such as a modification in second messenger concentration (preferably calcium ions or inositol phosphates such as $IP_3$) or a modification in the cellular metabolism (preferably determined by the acidification rate of the culture medium), a decrease in the peptide activity, thereby determining whether the ligand is a peptide antagonist.

The present invention relates to a method for determining whether a ligand is an antagonist of the peptide according to the invention, which comprises preparing a cell extract from cells transfected with an expressing the nucleic acid molecule encoding said peptide, isolating a membrane fraction from the cells extract, contacting the membrane fraction with the ligand in the presence of a known peptide agonist, under conditions permitting the activation of a functional peptide response and detecting by means of a bio-assay, such as a modification in the production of a second messenger, a decrease in the peptide activity, thereby determining whether the ligand is a peptide antagonist.

Preferably, the second messenger assay comprises measurement of calcium ions or inositol phosphates such as $IP_3$.

Preferably, the cell used in said method is a mammalian cell non neuronal in origin, such as CHO-K1, HEK293, BHK21, COS-7 cells.

In said method, the ligand is not previously known.

The invention is also related to the ligand isolated and detected by any of the preceding methods.

The present invention concerns also the pharmaceutical composition which comprises an effective amount of an agonist or an antagonist of the peptide according to the invention, effective to reduce the activity of said peptide and a pharmaceutically acceptable carrier.

It is meant by "an agonist or an antagonist of the peptide according to the invention", all the agonists or antagonists of the known "natural ligand" of the peptide as above described.

Therefore, the previously described methods may be used for the screening of drugs to identify drugs which specifically bind to the peptide according to the invention.

The invention is also related to the drugs isolated and detected by any of these methods.

The present invention concerns also a pharmaceutical composition comprising said drugs and a pharmaceutically acceptable carrier.

The invention is also related to a method of detecting expression of a peptide according to the invention by detecting the presence of MRNA coding for a peptide, which comprises obtaining total RNA or total MRNA from the cell and contacting the RNA or MRNA so obtained with the nucleic acid probe according to the invention under hybridizing conditions and detecting the presence of MRNA hybridized to the probe, thereby detecting the expression of the peptide by the cell.

Said hybridization conditions are stringent conditions.

The present invention concerns also the use of the pharmaceutical composition according to the invention for the treatment and/or prevention of inflammatory diseases, including rheumatoid arthritis, glomerulonephritis, asthma, idiopathic pulmonary fibrosis and psoriasis, viral infections including Human Immunodeficiency Viruses 1 and 2 (HIV-1 and 2), cancer including leukaemia, atherosclerosis and/or auto-immune disorders.

The present invention concerns also a method for diagnosing a predisposition or a resistance to a disorder associated with the activity of the peptide according to the invention and/or associated with infectious agents such as HIV viruses in a subject. Said method comprises
a) obtaining nucleic acid molecules encoding the peptide according to the invention from the cells of the subject;
b) possibly performing a restriction digest of said nucleic acid molecules with a panel of restriction enzymes;
c) possibly electrophoretically separating the resulting nucleic acid fragments on a sized gel;
d) contacting the resulting gel or the obtained nucleic acid molecule with a nucleic acid probe labelled with a detectable marker and capable of specifically hybridizing to said nucleic acid molecule (said hybridization being made in stringent hybridization conditions);
e) detecting labelled bands or the in situ nucleic acid molecules which have hybridized to the said nucleic acid molecule labelled with a detectable marker to create a unique band pattern or an in situ marking specific to the subject;
f) preparing other nucleic acid molecules encoding the peptide according to the invention obtained from the cells of other patients for diagnosis by step a-e; and
g) comparing the unique band pattern specific to the nucleic acid molecule of subjects suffering from the disorder from step e and the nucleic acid molecule obtained for diagnosis from step f to determine whether the patterns are the same or different and to diagnose thereby a predisposition or a resistance to the disorder if the patterns are the same or different.

The present invention is also related to a method for diagnosing a predisposition or a resistance to a disorder associated with the activity of a specific allele of the peptide according to the invention or the presence of said peptide at the surface of cells and/or associated with infectious agents such as HIV viruses present in a subject. Said method comprises:
a) obtaining a sample of a body fluid, preferably a blood sample comprising antigen presenting cells, from a subject;
b) adding to said sample a ligand and/or an anti-ligand according to the invention;
c) detecting the cross-reaction between said ligand and/or said anti-ligand and the specific peptide according to the invention; and
d) determining whether the peptide corresponds to a receptor or an inactive receptor according to the invention and diagnosing thereby a predisposition or a resistance to the disorder according to the type of the peptide present in the body fluid of the subject.

The present invention concerns also a diagnostic and/or dosage device, preferably a kit, comprising the peptides, the nucleic acid molecules, the nucleic acid probes, the ligands and/or the anti-ligands according to the invention, their portions (such as primers, probes, epitopes, . . . ) or a mixture thereof, being possibly labelled with a detectable marker.

Said diagnostic and/or dosage device comprises also the reactants for the detection and/or the dotage of antigens, antibodies or nucleic acid sequences through a method selected from the group consisting of in situ hybridization, hybridization or recognition by marked specific antibodies, specially ELISA® (Enzyme Linked Immunosorbent Assay) or RIA® (Radio Immunoassay), methods on filter, on a solid support, in solution, in "sandwich", on gel, by Dot blot hybridization, by Northern blot hybridization, by Southern blot hybridization, by isotopic or non-isotopic labelling (such as immunofluorescence or biotinylation), by a technique of cold probes, by genetic amplification, particularly PCR, LCR, NASBA or CPR, by a double immunodiffusion, by a counter-immunoelectrophoresis, by haemagglutination and/or a mixture thereof.

A last aspect of the present invention concerns a method of preparing peptides according to the invention, which comprises
a) constructing a vector adapted for expression in a cell which comprises the regulatory elements necessary for the expression of nucleic acid molecules in the cell operatively linked to nucleic acid molecule encoding said peptide so as to permit expression thereof, wherein the cell is preferably selected from the group consisting of bacterial cells, yeast cells, insect cells and mammalian cells;
b) inserting the vector of step a in a suitable host cell;
c) incubating the cell of step b under conditions allowing the expression of the peptide according to the invention;
d) recovering the peptide so obtained; and
e) purifying the peptide so recovered, thereby preparing an isolated peptide—according to the invention.

The deposits of micro-organisms AchCCR5-SAB1A7 and CHO-K1-PEFIN HCCR5-1/16 were made according to the Budapest Treaty in the Belgium Coordinated Collection of Micro-organisms (BCCM), Laboratorium voor Moleculaire Biologic (LMBP), Universiteit Gent, K. L. Ledeganckstraat 35, B-9000 GENT, BELGIUM.

BRIEF DESCRIPTION OF THE FIGURES

FIG. 1 Shows the nucleic acid and amino acid sequences of the invention. FIG. 1A-1 and 1A-2 show the nucleic acid and amino acid sequence of SEQ ID No.s 1 and 4, respectively. FIG. 1B-1, 1B-2, and 1B-3 show the nucleic acid and amino acid sequence of SEQ ID Nos. 2 and 5, respectively. FIG. 1D-1 to 1D-3 show the nucleic acid and amino acid sequence of SEQ ID Nos. 3 and 6, respectively.

FIG. 2 represents the amino acids sequence of the active human CCR5 chemokine receptor (SEQ ID NO: 5) according to the invention aligned with that of the human CCR1 (SEQ ID NO: 9), CCR2b (SEQ ID NO: 7), CCR3 (SEQ ID NO: 8), and CCR4 (SEQ ID NO: 10) receptors. Amino acids identical with the active CCR5 sequence are boxed.

FIG. 3 shows the chromosomal organisation of the human CCR2 and CCR5 chemokine receptor genes.

FIG. 6 represents the structure of the mutant form of human CCR5 receptor. FIG. 6B shows the wild type amino acid sequence (SEQ ID NO: 11), and the location of the 32 base deletion mutation in the nucleic acid (SEQ ID NO: 12) and amino acid sequences (SEQ ID NO: 13).

DETAILED DESCRIPTION OF THE PREFERRED EMBODIMENTS

1. Experimentals

Materials

Figure 3:
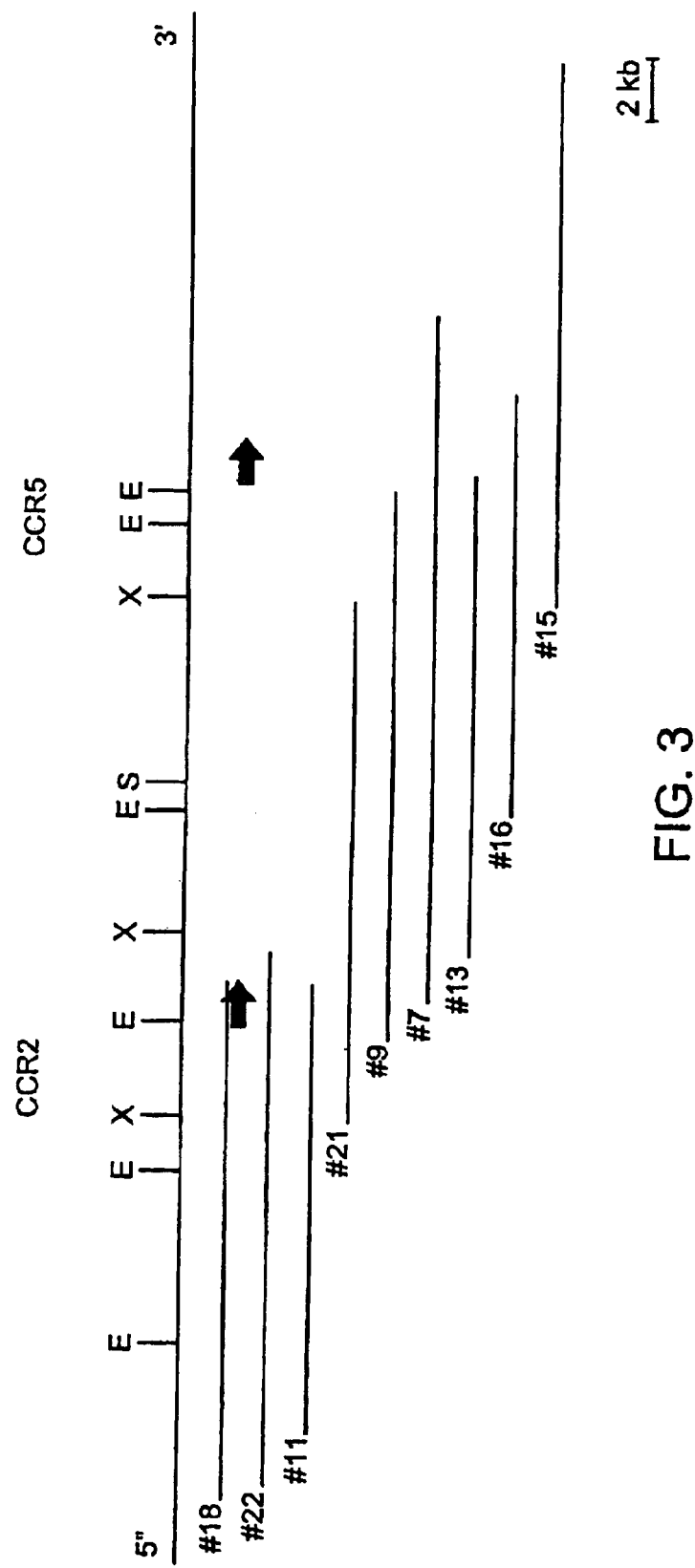

Recombinant human chemokines, including MCP-1, MIP-1α, MIP-1β, RANTES, IL-8 and GROα were obtained from R & D Systems (London, UK). [$^{125}$I]MIP-1α (specific activity, 2200 Ci/mmol) was obtained from Dupont NEN (Brussels, Belgium). Chemokines obtained from R & D Systems were reported by the supplier as >97% pure on SDS-PAGE (sodium dodecyl sulphate-polyacrylamide gel electrophoresis) and biologically active on a bioassay specific for each ligand. The lyophilised chemokines were dissolved as a 100 μg/ml solution in a sterile phosphate-buffered saline (PBS) and this stock solution was stored at −20° C. in aliquots. Chemokines were diluted to the working concentration immediately before use. All cell lines used in the present study were obtained from the ATCC (Rockville, Md., USA).

Cloning and Sequencing

The mouse MOP020 clone was obtained by low stringency polymerase chain reaction, as described previously [24, 34], using genomic DNA as template. A human genomic DNA library (Stratagene, La Jolla, Calif.), constructed in the lambda DASH vector was screened at low stringency [39] with the MOP020 (511 bp) probe. The positive clones were purified to homogeneity and analysed by Southern blotting. The restriction map of the locus was determined and a relevant XbaI fragment of 4,400 bp was subcloned in pBluescript SK+ (Stratagene). Sequencing was performed on both strands after subcloning in M13mp derivatives, using fluorescent primers and an automated DNA sequencer (Applied Biosystem 370A). Sequence handling and data analysis was carried out using the DNASIS/PROSIS software (Hitachi), and the GCG software package (Genetics Computer Group, Wisconsin).

Expression in Cell Lines

The entire coding region was amplified by PCR as a 1056 bp fragment, using primers including respectively the BamHI and XbaI recognition sequences, and cloned after restriction in the corresponding sites of the eukaryotic expression vector pcdna3 (Invitrogen, San Diego, Calif.). The resulting construct was verified by sequencing, and transfected in CHO-K1 cells as described [35]. Two days after transfection, selection for stably transfected cell lines was initiated by the addition of 400 μg/ml G418 (Gibco), arid resistant clones were isolated at day 10. CHO-K1 cells were cultured using Ham's F12 medium, as previously described [35, 11]. The expression of the active CCR5 receptor in the various cell clones was evaluated by measuring the specific transcript level by Northern blotting, on total RNA prepared from the cells (see below).

Binding Assays

Stably transfected CHO-K1 cells expressing the active CCR5 receptor were grown to confluence and detached from culture dishes by incubation in phosphate-buffered saline (PBS) supplemented with 1 Mm EDTA. Cells were collected by low speed centrifugation and counted in a Neubaeur cell. Binding assays were performed in polyethylene minisorp tubes (Nunc) in a final volume of 200 μl PBS containing 0.2% bovine serum albumin (BSA) and $10^6$ cells, in presence of [$^{125}$I]-MIP-1α. Non specific binding was determined by addition of 10 Nm unlabelled MIP-1α. The concentration of labelled ligand was 0.4 Nm (around 100 000 cpm per tube). The incubation was carried out for 2 hours at 4° C., and was: stopped by the rapid addition of 4 ml ice-cold buffer, and immediate collection of cells by vacuum filtration through GF/B glass fiber filters (Whatmann) pre-soaked in 0.5% polyethyleneinimine (Sigma). Filters were washed three times with 4 ml ice-cold buffer and counted in a gamma counter.

Biological Activity

The CHO-K1 cell lines stably transfected with the pcdna3/CCR5 construct or wild type CHO-K1 cells (used as controls) were plated onto the membrane of Transwell cell capsules (Molecular Devices), at a density of 2.5 $10^5$ cells/well in Ham's F12 medium. The next day, the capsules were transferred in a microphysiometer (Cytosensor, Molecular Devices), and the cells were allowed to equilibrate for approximately two hours by perfusion of 1 Mm phosphate-buffered (Ph 7.4) RPMI-1640 medium containing 0.2% BSA. Cells were then exposed to various chemokines diluted in the same medium, for a 2 mm duration. Acidification rates were measured at one minute intervals.

Northern Blotting

Total RNA was isolated from transfected CHO-K1 cell lines, from a panel of human cell lines of haematopoietic origin and from a panel of dog tissues, using the RNeasy kit (Qiagen). RNA samples (10 μg per lane) were denatured in presence of glyoxal [26], fractionated on a 1% agarose gel in a 10 Mm phosphate buffer (Ph 7.0), and transferred to nylon membranes (Pall Biodyne A, Glen Cove, N.Y.) as described [42]. After baking, the blots were prehybridized for 4 h at 42° C. in a solution consisting of 50% formamide, 5× Denhardt solution (1× Denhardt: 0.02% Ficoll, 0.02% polyvinylpyrolidone, 0.02% BSA), 5×SSPE (1×SSPE: 0.18 M NaCl, 10 Mm Na phosphate, 1 Mm EDTA Ph 8.3), 0.3% Sodium Dodecyl Sulphate (SDS), 250 μg per ml denatured DNA from herring testes. DNA probes were ($\alpha^{32}$P)-labelled by random priming [14]. Hybridizations were carried out for 12 h at 42° C. in the same solution containing 10% (wt/vol) dextran sulphate and the heat denatured probe. Filters were washed up to 0.1×SSMC (1×SSC: 150 Mm NaCl, 15 Mm Na Citrate Ph 7.0), 0.1% SDS at 60° C. and autoradiographed at −70° C. using Amersham β-max films.

2. Results and Discussion

Cloning and Structural Analysis

The sequence homology characterising genes encoding G protein-coupled receptors has allowed the cloning by low stringency polymerase chain reaction (PCR) of new members of this gene family [24, 34]. One of the clones amplified from mouse genomic DNA, named MOP020 presented strong similarities with characterised chemokine receptors, sharing 80% identity with the MCP-1 receptor (CCR2) [8], 65% identity with the MIP-1α/RANTES receptor (CCR1) [31], and 51% identity with IL-8 receptors [20, 30]. The clone was used as a probe to screen a human genomic library. A total of 16 lambda phage clones were isolated. It was inferred from the restriction pattern of each clone and from partial sequence data that all clones were belonging to a single contig in which two different coding sequences were included. One of the coding sequences was identical to the reported CDNA encoding the CCR2 receptor [8, 44]. A 4.400 pb XbaI fragment of a representative clone containing the second region of hybridization was subcloned in Pbluescript SK+. Sequencing revealed a novel gene, tentatively named CCR5, sharing 84% identity with the MOP020 probe, suggesting that MOP020 is the mouse ortholog of CCR5. MOP020 does not correspond to any of the three mouse chemokine receptor genes cloned recently [16], demonstrating the existence of a fourth murine chemokine receptor.

Figure 2B:
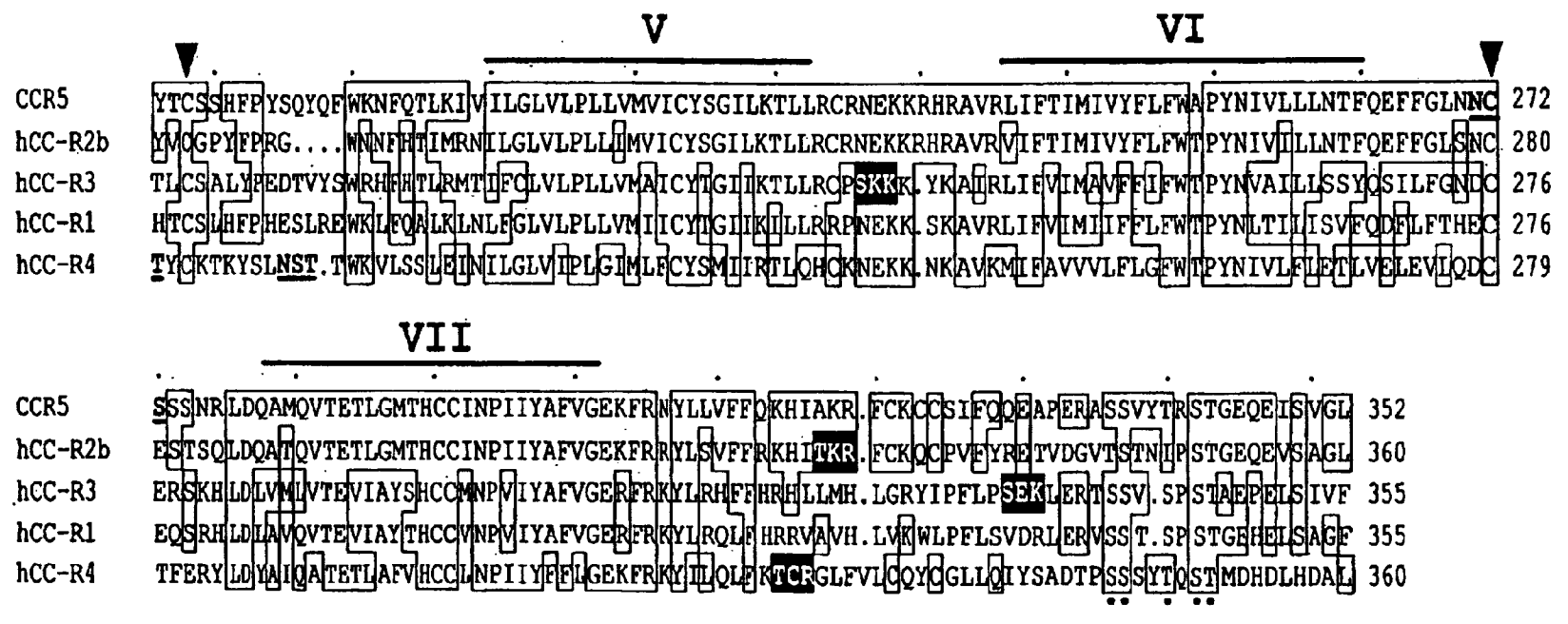

The sequence of CCR5 revealed a single open reading frame of 352 codons encoding a protein of 40,600 Da. The sequence surrounding the proposed initiation codon is in agreement with the consensus as described by Kozak [22], since the nucleotide in −3 is a purine. The hydropathy profile of the deduced amino acid sequence is consistent with the existence of 7 transmembrane segments. Alignment of the CCR5 amino acid sequence with that of other functionally characterised human CC-chemokine receptors is represented in FIG. 2. The highest similarity is found with the CCR2 receptor [8] that shares 75.8% identical residues. There is also 56.3% identity with the CCR1 receptor [31], 58.4% with the CCR3 [10], and 49.1% with the CCR4 [37]. CCR5 represents therefore a new member of the CC-chemokine receptor group [30]. Like the related CCR1 and IL-8 receptors [20, 29, 31, 16] the coding region of CCR5 appears as intronless. From our partial sequencing data, the CCR2 gene is also devoid of intron in the first two thirds of its coding sequence.

Sequence similarities within the chemokine receptor family are higher in the transmembrane-spanning domains, and in intracellular loops. As an example, the identity score between CCR5 and CCR2 goes up to 92% when considering the transmembrane segments only. Lower similarities are found in the N-terminal extracellular domain, and in the extracellular loops. The N-terminal domain of the IL-8 and CCR2 receptors has been shown to be essential for interaction with the ligand [19, 18]. The variability of this region among CC-chemokine receptors presumably contributes to the specificity towards the various ligands of the family.

A single potential site for N-linked glycosylation was identified in the third extracellular loop of CCR5 (FIG. 1). No glycosylation site was found in the N-terminal domain of the receptor, where most G protein-coupled receptors are glycosylated. The other chemokine receptors CCR1 and CCR2 present such an N-linked glycosylation site in their N-terminal domain [31, 8]. By contrast, the CCR3 receptor [10] does not display glycosylation sites neither in the N-terminus, nor in extracellular loops. The active CCR5 receptor has four cysteines in its extracellular segments, and all four are conserved in the other CC- and CXC-chemokine receptors (FIG. 2). The cysteines located in the first and second extracellular loops are present in most G protein-coupled receptors, and are believed to form a disulphide bridge stabilising the receptor structure [41]. The two other cysteines, in the N-terminal segment, and in the third extracellular loop could similarly form a stabilising bridge specific to the chemokine receptor family. The intracellular domains of CCR5 do not include potential sites for phosphorylation by protein kinase C (PKC) or protein kinase A. PKC sites, involved in heterologous desensitisation are frequent in the third intracellular loop and C-terminus of G protein-coupled receptors. CCR1 is also devoid of PKC sites. In contrast, all CC-chemokine receptors, are rich in serine and threonine residues in the C-terminal domain. These residues represent potential phosphorylation sites by the family of G protein-coupled receptor kinases, and are probably involved in homologous desensitisation [41]. Five of these S/T residues are perfectly aligned in all five receptors (FIG. 2).

Physical Linkage of the CCR5 and CCR2 Genes

As stated above, the 16 clones isolated with the MOP020 probe corresponded to a single contig containing the CCR5 and CCR2 genes. The organisation of this contig was investigated in order to characterise the physical linkage of the two receptor genes in the human genome. A combination of restriction mapping, Southern blotting, fragment subcloning and partial sequencing allowed to determine the respective borders and overlaps of all clones. Out of the 16 clones, 9 turned out to be characterised by a specific restriction map, and their organisation is depicted in FIG. 3. Four of these clones (#11, 18, 21, 22) contained the CCR2 gene alone, four clones (# 7, 13, 15, 16) contained the ChemR13 gene alone and one clone (#9) contains part of both coding sequences. The CCR2 and CCR5 genes are organised in tandem, CCR5 being located downstream of CCR2. The distance separating CCR2 and CCR5 open reading frames is 17.5 kb. The chromosomal localisation of the tandem is presently unknown. Other chemokine receptors have however been located in the human genome: the CCR1 gene was localised by fluorescence in situ hybridization to the p21 region of human chromosome 3 [16]. The two IL-8 receptor genes, and theft pseudogene have been shown to be clustered on the human 2q34-q35 region [1].

Functional Expression and Pharmacoloy of the Active CCR5 Receptor

Stable CHO-K1 cell lines expressing the active CCR5 receptor were established and were screened on the basis of the level of CCR5 transcripts as determined by Northern blotting. Three clones were selected and tested for biological responses in a microphysiometer, using various CC- and CXC-chemokines as potential agonists. Wild type CHO-K1 dells were used as control to ensure that the observed responses were specific for the transfected receptor, and did not result from the activation of endogenous receptors. The microphysiometer allows the real time detection of receptor activation, by measuring the modifications of cell metabolism resulting from the stimulation of intracellular cascades [33]. Several studies have already demonstrated the potential of microphysiometry in the field of chemokine receptors. Modifications of metabolic activity in human monocytes, in response CC-chemokines, were monitored using this system [43]. Similarly, changes in the acidification rate of THP-1 cells (a human monocytic cell line) in response to MCP-1 and MCP-3 have been measured [36]. The estimation of the $EC_{50}$ for both proteins, using this procedure, was in agreement with the values obtained by monitoring the intracellular calcium in other studies [8, 15].

Figure 4A:
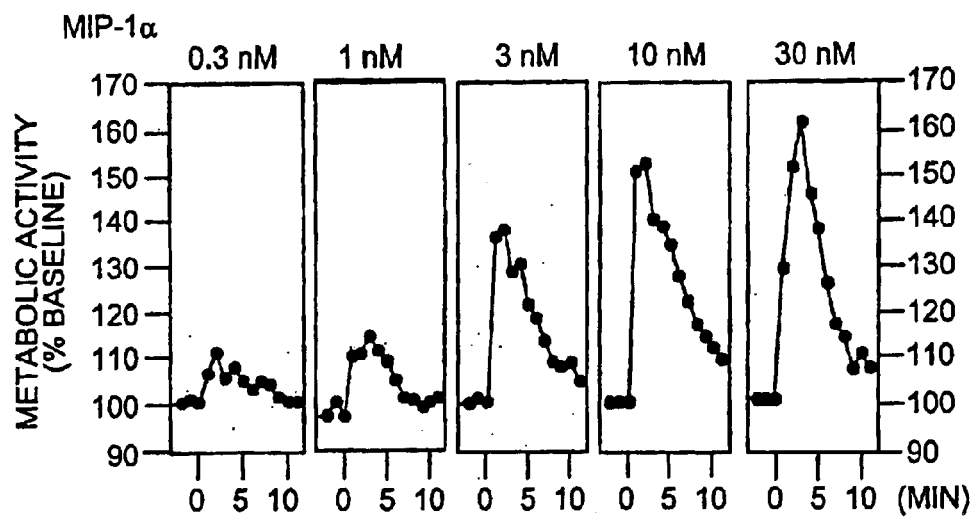
FIG. 4 shows the functional expression of the human active CCR5 receptor in a CHO-K1 cell line.
Figure 4B:
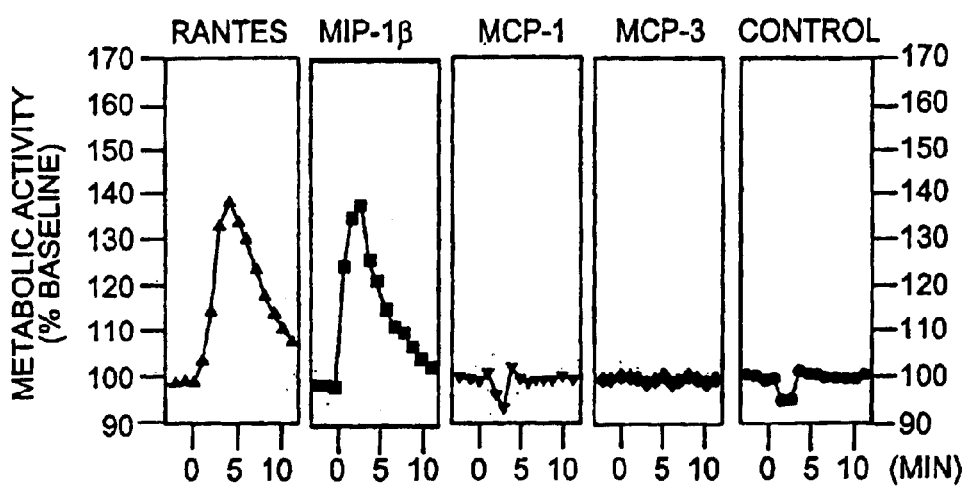
Figure 4C:
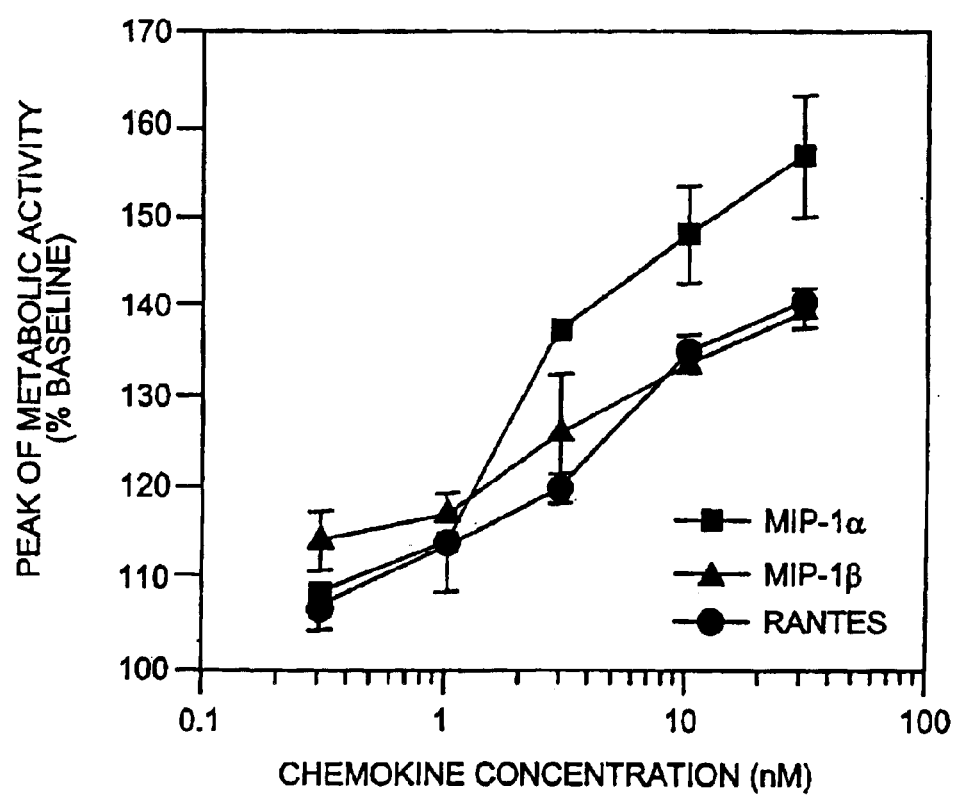

Ligands belonging to the CC- and CXC-chemokine classes were tested on the CCR5 transfected CHO-K1 cells. Whereas MIP-1α, MIP-1β and RANTES were found to be potent activators of the new receptor (FIG. 4), the CC-chemokines MCP-1, MCP-2 and MCP-3, and the CXC-chemokines GROα and IL-8 had no effect on the metabolic activity, even at the highest concentrations tested (30 Nm). The biological activity of one of the chemokines inducing no response on CCR5 (IL-8) could be demonstrated on a CHO-K1 cell line transfected with the IL-8A interleukin receptor (Mollereau et al., 1993): IL-8 produced a 160% increase in metabolic activity as determined using the microphysiometer. The biological activity of the MCP-2 and MCP-3 preparations as provided by J. Van Damme have been widely documented [2, 40]. MIP-1α, MIP-1β and RANTES were tested on the wild type CHO-K1 cells, at a 30 Nm-concentration, and none of them induced a metabolic response. On the CCR5 transfected CHO-K1 cell line, all three active ligands (MIP-1α, MIP-1β and RANTES) caused a rapid increase in acidification rate, reaching a maximum by the second or third minute after perfusion of the ligand. The acidification rate returned to basal level within 10 minutes. The timing of the cellular response is similar to that observed for chemokines on their natural receptors in human monocytes [43]. When agonists were applied repeatedly to the same cells, the response was strongly reduced as compared to the first stimulation, suggesting the desensitisation of the receptor. All measurements were therefore obtained on the first stimulation of each capsule.

The concentration-effect relation was evaluated for the three active ligands in the 0.3 to 30 Nm range (FIGS. 3B and C). The rank order of potency was MIP-1α>MIP-1β=RANTES. At 30 Nm concentrations, the effect of MIP-1α appeared to saturate (at 156% of baseline level) while MIP-1β and RANTES were still in the ascending phase. Higher concentrations of chemokines could however not be used. The EC50 was estimated around 3 Nm for MIP-1α. The concentrations necessary for obtaining a biological response as determined by using the microphysiometer are in the same range as those measured by intracellular calcium mobilisation for the CCR1 [31], the CCR2A and B [8], and the CCR3 [10] receptors. The ligand specificity of CCR5 is similar to that reported for CCR3 [10]. CCR3 was described as the first cloned receptor responding to MIP-1β. However, MIP-1β at 10 Nm elicits a significant effect on the CCR5, while the same concentration is without effect on the CCR3 transfected cells [10]. These data suggest that CCR5 could be a physiological receptor for MIP-1β.

Binding experiments using [$^{125}$I]-human MIP-1α a as ligand did not allow to demonstrate specific binding to CCR53 expressing CHO-K1 cells, using as much as 0.4 Nm radioligand and 1 million transfected cells per tube. Failure to obtain binding data could be attributed to a relatively low affinity of the receptor for MIP-1α.

Northern Blotting Analysis

Figure 5:
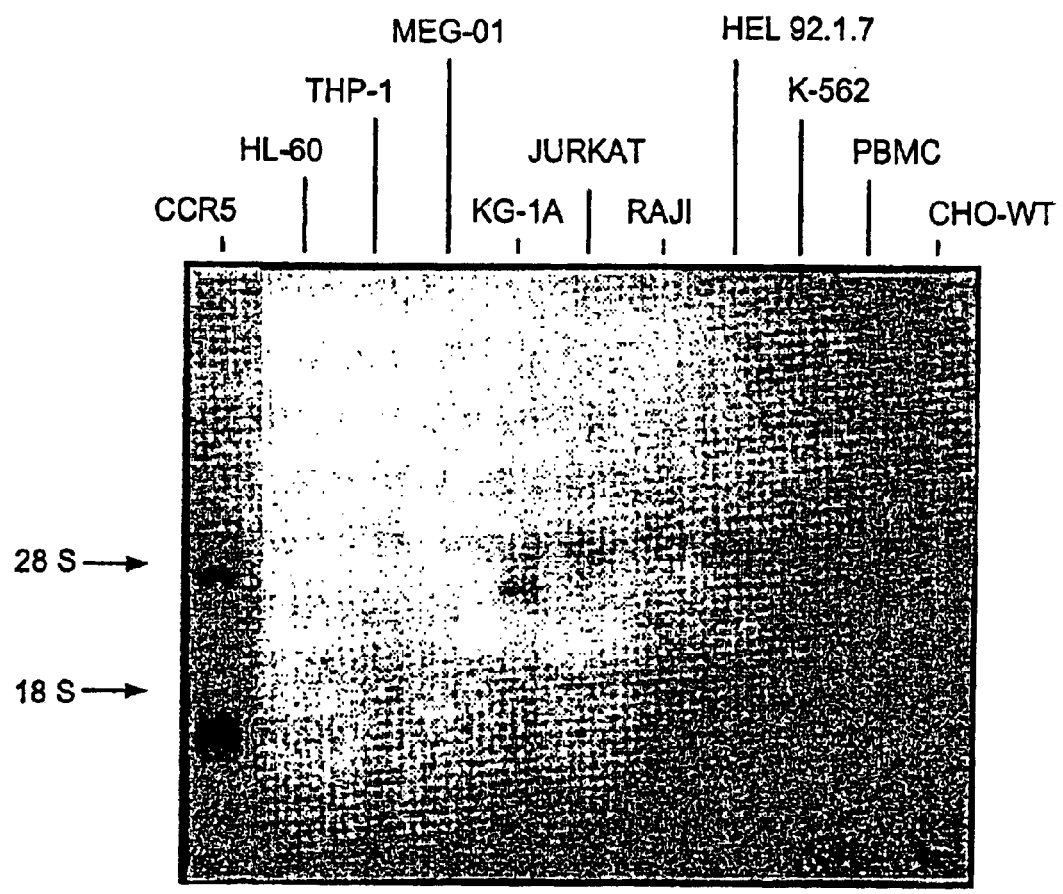
FIG. 5 represents the distribution of MRNA encoding the CCR5 receptor in a panel of human cell lines of haematopoietic origin.

Northern blotting performed on a, panel of dog tissues did not allow to detect transcripts for CCR5. Given the role of the chemokine receptor family in mediating chemoattraction and activation of various classes of cells involved in inflammatory and immune responses, the probe was also used to detect specific transcripts in a panel of human cell lines of haematopoietic origin (FIG. 5). The panel included lymphoblastic (Raji) and T lymphoblastic (Jurkat) cell lines, promyeloblastic (KG-1A) and promyelocytic (HL-60) cell lines, a monocytic (THP-1) cell line, an erythroleukemia (HEL 92.1.7) cell line, a megakaryoblastic (MEG-01) cell line, and a myelogenous leukaemia (K-562) cell line. Human peripheral blood mononuclear cells (PBMC), including mature monocytes and lymphocytes, were also tested. CCR5 transcripts (4.4 kb) could be detected only in the KG-1A promyeloblastic cell line, but were not found in the promyelocytic cell line HL-60, in PBMC, or in any of the other cell lines tested. These results suggest that the active CCR5 receptor could be expressed in precursors of the granulocytic lineage. CC-chemokines have been reported to stimulate mature granulocytes [27, 38, 23, 2]. However, recent data have also demonstrated a role of CC- and CXC-chemokines in the regulation of mouse and human myeloid progenitor cell proliferation [6, 7].

CCR5 was shown to respond to MIP-1α, MIP-1β and RANTES, the three chemokines identified as the major HIV-suppressive factors produced by CD8$^+$ T cells [9], and released in higher amounts by CD4$^+$ T lymphocytes from uninfected but multiply exposed individuals [51]. CCR5 represents a major co-receptor for macrophage-tropic (M-tropic) HIV-1 primary isolates and strains [45, 50]. M-tropic strains predominate during the asymptomatic phase of the disease in infected individuals, and are considered as responsible for HIV-1 transmission. Strains adapted for growth in transformed T-cell lines (T-tropic strains) use as a co-receptor LESTR (or fusin) [50], an orphan receptor also belonging to the chemokine receptor family, but not yet characterized functionally [21, 52, 53]. Dual-tropic viruses, which may represent transitional forms of the virus in late stages of infection [54] are shown to use both CCR5 and LESTR as co-receptors, as well as the CC-chemokine receptors CCR2b and CCR3 [47]. The broad spectrum of co-receptor usage of dual-tropic viruses suggests that within infected individuals, the virus may evolve at least in part from selection by a variety of co-receptors expressed on different cell types.

Identification of an Inactive ΔCCR5 Receptor

Figure 6A:
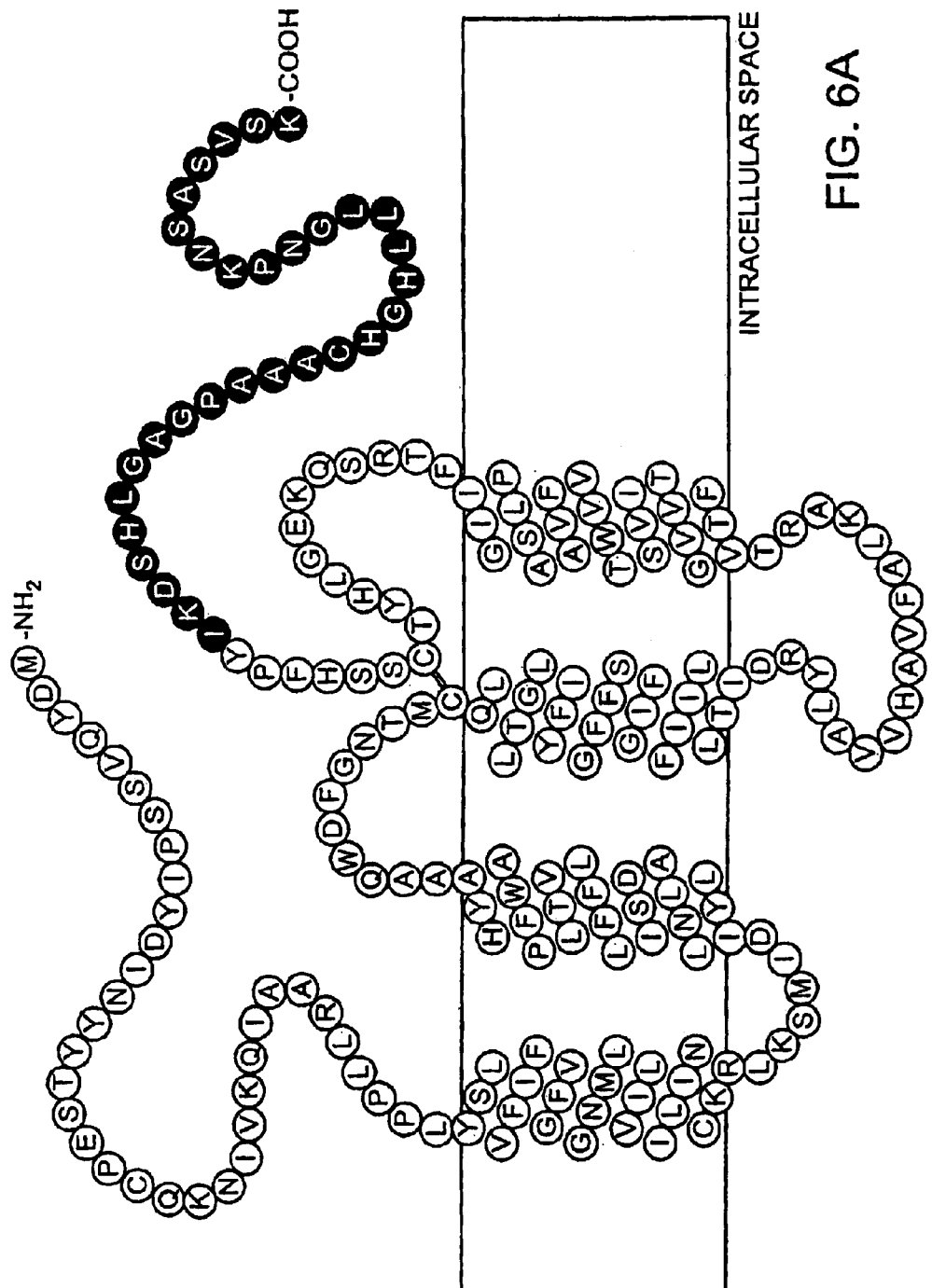
FIG. 6A shows a diagram of the mutant form of human CCR5 receptor (SEQ ID NO:18) situated in a membrane.

It is known that some individuals remain uninfected despite repeated exposure to HIV-1 [55, 56, 51]. A proportion of these exposed-uninfected individuals results from the relatively low risk of contamination after a single contact with the virus, but it has been postulated that truly resistant individuals do exist. In fact, CD4$^+$ lymphocytes isolated from exposed-uninfected individuals are highly resistant to infection by primary M-tropic, but not T-tropic HIV-1 strains. Also, peripheral blood mononuclear cells (PBMC) from different donors are not infected equally with various HIV-1 strains [57–59]. Given the key role played by CCR5 in the fusion event that mediates infection by M-tropic viruses, it is postulated that variants of CCR5 could be responsible for the relative or absolute resistance to HIV-1 infection exhibited by some individuals, and possibly for the variability of disease progression in infected patients [66]. The Inventors selected three HIV-1 infected patients known to be slow progressors, and four seronegative individuals as controls; the full coding region of their CCR5 gene was amplified by PCR and sequenced. Unexpectedly, one of the slow progressors, but also two of the uninfected controls, exhibited heterozygosity at the CCR5 locus for a biallelic polymorphism. The frequent allele corresponded to the published CCR5 sequence, while the minor one displayed a 32 bp deletion within the coding sequence, in a region corresponding to the second extracellular loop of the receptor (FIG. 6). The FIG. 6 is the structure of the mutant form of human CC-chemokine receptor 5. α, The amino acid sequence of the non-functional Δccr5 protein is represented. The transmembrane organisation is given by analogy with the predicted transmembrane structure of the wild-type CCR5. Amino acids represented in black correspond to unnatural residues resulting from the frame shift caused by the deletion. The mutant protein lacks the last three transmembrane segments of CCR5, as well as the regions involved in G protein-coupling b, Nucleotide sequence of the CCR5 gene surrounding the deleted region, and translation into the normal receptor (top) or the truncated mutant (ccr5, bottom). The 10-bp direct repeat is represented in italics. The full size coding region of the CCR5 gene was amplified by PCR, using 5'-TCGAGGATCCAAGATG GATTATCAAGT-3' (SEQ ID NO: 14) and 5'-CTGATCTAG AGCCATGTGCACAACTCT-3' (SEQ ID NO: 15) as forward and reverse primers' respectively. The PCR products were sequenced on both strands using the same oligonucleotides as primers, as well as internal primers, and fluorochrome-labelled dideoxynucleotides as terminators. The sequencing products were run on an Applied Biosystem sequencer, and ambiguous positions were searched along the coding sequence. When the presence of a deletion was suspected from direct sequencing, the PCR products were cloned after restriction with BamHI and XbaI endonucleases into pcdna3. Several clones were sequenced to confirm the deletion. The deletion was identical in three unrelated individuals investigated by sequencing.

Figure 7A:
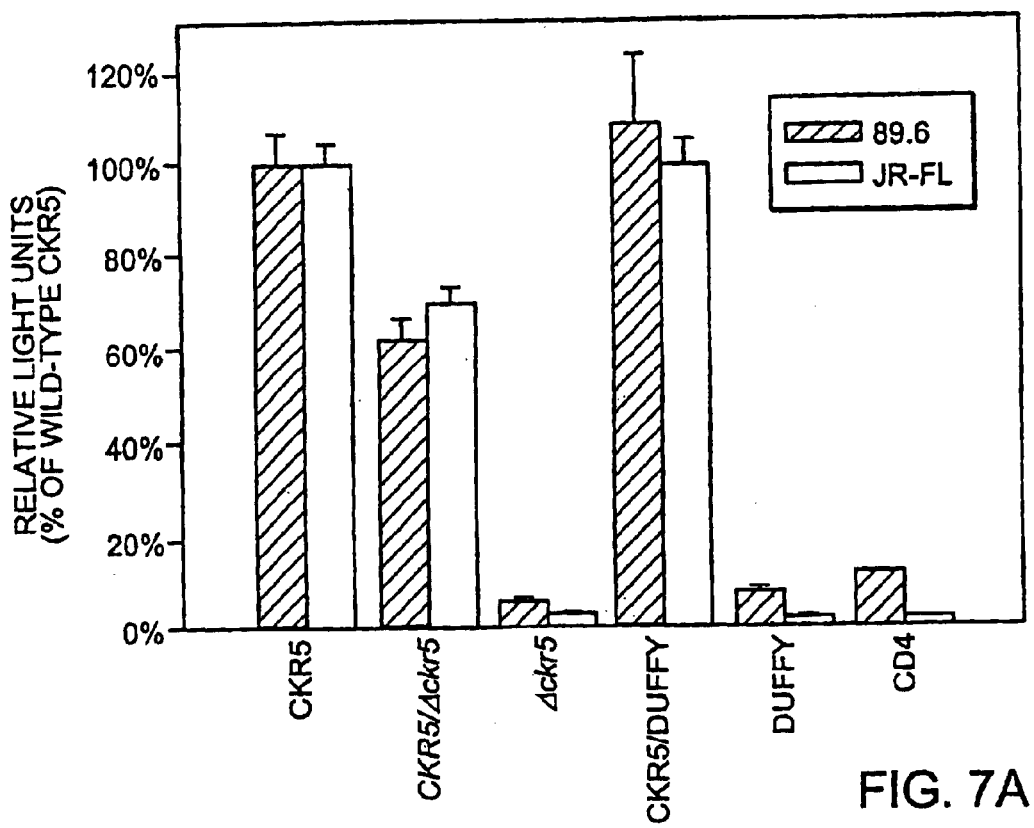
FIG. 7 represents the quantification of ENV proteins-mediated fusion by luciferase assays.
Figure 7B:
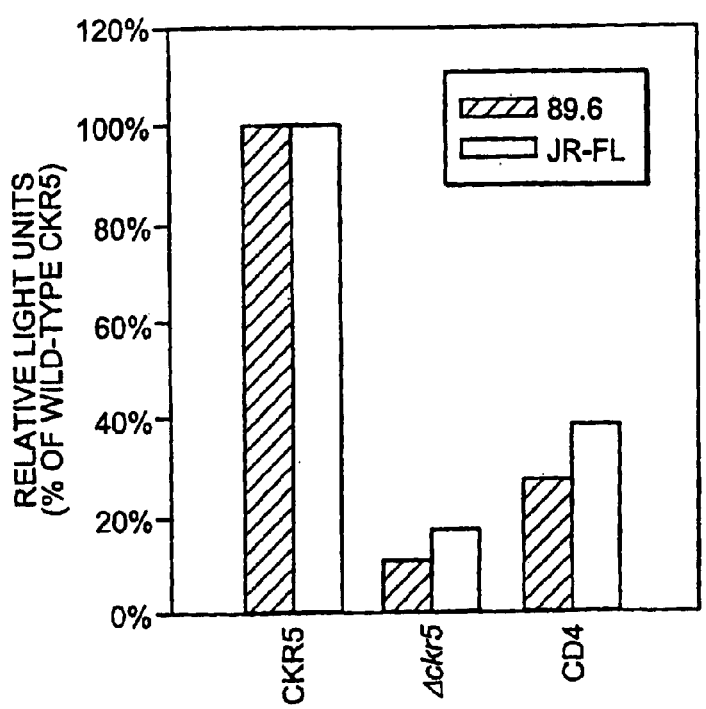

Cloning of the PCR product and sequencing of several clones confirmed the deletion. The deletion causes a frame shift, which is expected to result in premature termination of translation. The protein encoded by this mutant allele (Δccr5) therefore lacks the last three transmembrane segments of the receptor. A 10-bp direct repeat flanking the deleted region (FIG. 6b) on both sides is expected to have promoted the recombination event leading to the deletion. Numerous mutagenesis studies performed on various classes of G protein-coupled receptors, including chemokine receptors, makes it clear that such a truncated protein is certainly not functional in terms of chemokine-induced signal transduction it lacks the third intracellular loop and C-terminal cytoplasmic domains, the two regions involved primarily in G protein coupling [41]. In order to test whether the truncated protein was able to function as a HIV-1 co-receptor, the Inventors tested its ability to support membrane fusion by both primary M-tropic and dual-tropic virus ENV proteins. The recombinant protein was expressed in quail QT6 cells together with human CD4. The QT6 cells were then mixed with HeLa cells expressing the indicated viral ENV protein and the extent of cell-cell fusion measured using a sensitive and quantitative gene-reporter assay. In contrast to wild-type CCR5, the truncated receptor did not allow fusion with cells expressing the ENV protein from either M-tropic or dual-tropic viruses (FIG. 7). The FIG. 7 represents the quantification of ENV protein-mediated fusion by luciferase assay. To quantify cell-cell fusion events, Japanese quail QT6 fibrosarcoma cells were transfected or cotransfected as indicated with the pcdna3 vector (Invitrogen) containing the coding sequence for wild-type CCR5, the truncated ccr5 mutant, the CCR2b or the Duffy chemokine receptors, or with the PCDNA3 vector alone. The target cells were also transfected with human CD4 expressed from the CMV promoter and the luciferase gene under the control of the T7 promoter. HeLa effector cells were infected (MOI=10) with vaccinia vectors expressing T7-polymerase (vTF1.1) and either the JR-FL (vCB28) or 89.6 (vBD3) envelope proteins. The luciferase activity resulting from cell fusion is expressed as the percentage of the activity (in relative light units) obtained for wild-type CCR5. All transfections were performed with an identical quantity of plasmid DNA using pcdna3 as carrier when necessary. To initiate fusion, target and effector cells were mixed in 24 well plates at 37° C. in the presence of ara-C and rifampicin, and allowed to fuse for 8 hours. Cells were lysed in 150 μl of reporter lysis buffer (Promega) and assayed for luciferase activity according to the manufacturer's instructions (Promega).

Coexpression of Δccr5 with wild-type CCR5 consistently reduced the efficiency of fusion for both JR-FL and 89.6 envelopes, as compared with CCR5 alone. Whether this in vitro inhibitory effect (not shared by the chemokine receptor Duffy, used as control) also occurs in vivo is presently not known. Coexpression with the CCR2b receptor [31], which is the CC-chemokine receptor most closely related to CCR5 but does not promote fusion by M-tropic HIV-1 strains [48], did not rescue the mutation by formation of a hybrid molecule (FIG. 7).

Figure 8:
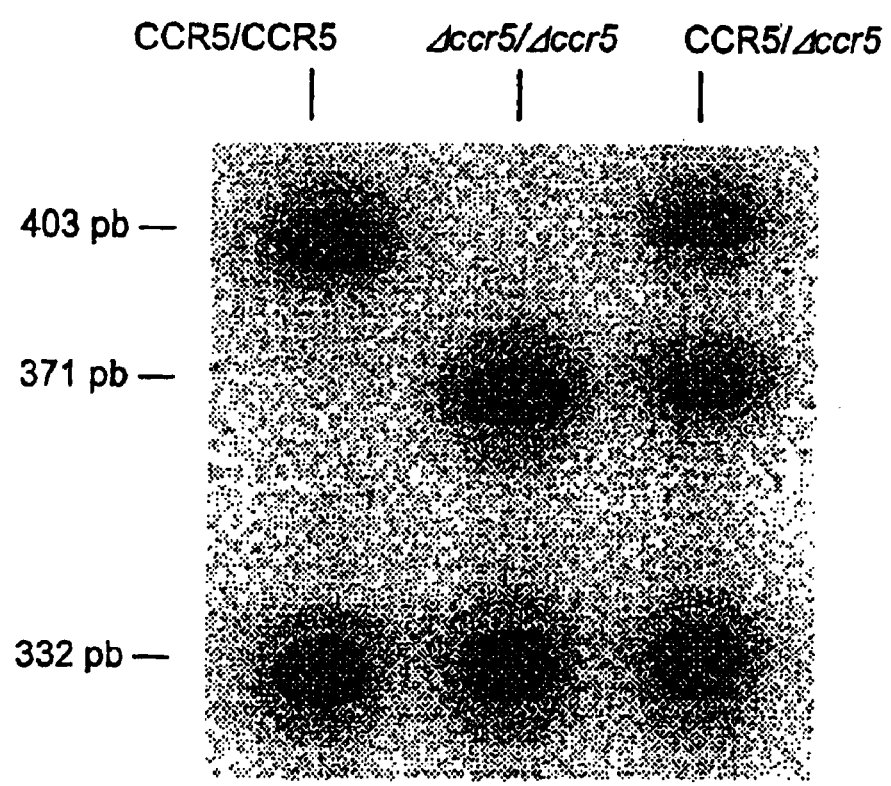
FIG. 8 represents genotyping of individuals by PCR and segregation of the CCR5 alleles in CEPH families.
Figure 9A:
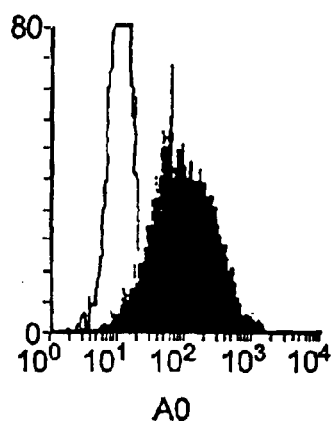
FIG. 9 represents the FACS analysis of sera anti-CCR5 on a CCR5-CHO cell line according to the invention.
Figure 9B:
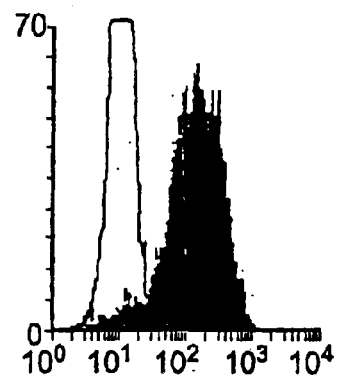
Figure 9C:
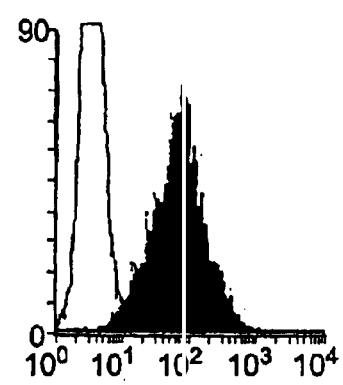
Figure 9D:
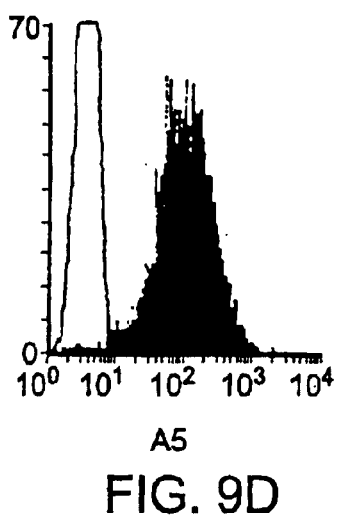
Figure 9E:
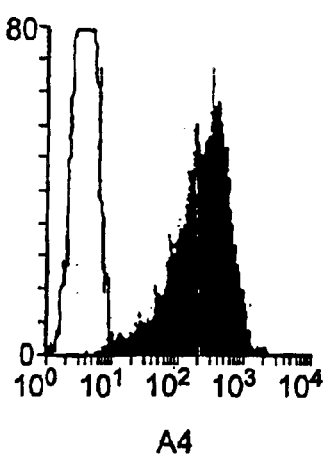
Figure 9F:
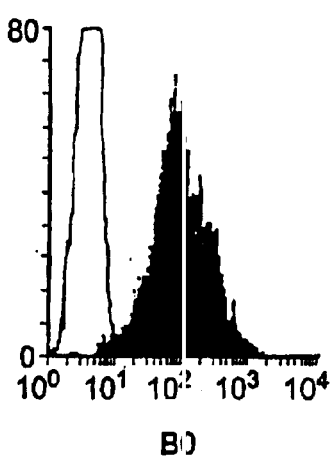
Figure 9G:
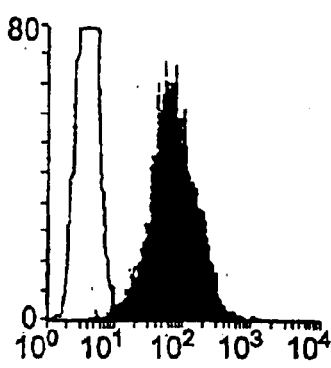
Figure 9H:
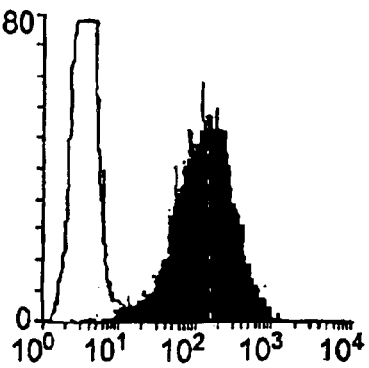

The FIG. 8 represents genotyping of individuals by PCR and segregation of the CCR5 alleles in CEPH families, α, Autoradiography illustrating the pattern resulting from PCR amplification and EcoRI cleavage for individuals homozygous for the wild-type CCR5 allele (CCR5/CCR5), the null Δccr5 allele (Δccr5/Δccr5), and for heterozygotes (CCR5/Δccr5). A 735 bp PCR product is cleaved into a common band of 332 bp for both alleles, and into 403 and 371 bp bands for the wild-type and mutant alleles, respectively. b, Segregation of the CCR5 alleles in two informative families of the CEPH. Half-black and white symbols represent heterozygotes and wild-type homozygotes, respectively. For a few individuals in the pedigrees, DNA was not available (ND: not determined). PCRs were performed on genomic DNA samples, using 5'-CCTGGCTGTCGTCCATGCTG-3' (SEQ ID NO: 16) and 5'-CTGATCTAGAGCCATGTGCAC AACTCT-3' (SEQ ID NO: 17) as forward and reverse primers respectively. Reaction mixtures consisted in 30 μl of 10 Mm Tris-HCl buffer pH 8.0, containing 50 Mm KCl, 0.75 Mm MgCl$_2$, 0.2 Mm dCTP, dGTP and dTTP, 0.1 Mm dATP, 0.5 μi [a-$^{32}$P]-dATP, 0.01% gelatin, 5% DMZ, 200 ng target DNA, 60 ng of each of the primers and 1.5 U Taq polymerase. PCR conditions were: 93° C. for 2 min 30; 93° C. for 1 min, 60° C. for 1 min, 72° C. for 1 min, 30 cycles; 72° C. for 6 min. After the PCR reaction, the samples were incubated for 60 min at 37° C. with 10 U EcoRI, and 2 μl of the denatured reaction mixture was applied onto a denaturing 5% polyacrylamide gel containing 35% formamide and 5.6 M urea. Bands were detected by autoradiography.

Based on the 14 chromosomes tested in the first experiment, the deleted Δccr5 allele appeared rather frequent in the Caucasian population. The accurate frequency was further estimated by testing (FIG. 8a) a large cohort of Caucasian individuals, including unrelated members of the CEPH (Centre d'Etude des Polymorphismes Humains) families, part of the IRIBHN staff, and a bank of anonymous DNA samples from healthy individuals collected by the Genetics Department of the Erasme Hospital in Brussels. From a total of more than 700 healthy individuals, the allele frequencies were found to be 0.908 for the wild-type allele, and 0.092 for the mutant allele (Table I). The genotype frequencies observed in the population were not significantly different from the expected Hardy-Weinberg distribution (CCR5/CCR5: 0.827 vs 0.824; CCR5/Δccr5: 0.162 vs 0.167; Δccr5/Δccr5: 0.011 vs 0.008, p>0.999), suggesting that the null allele has no drastic effect on fitness. Using two informative CEPH families, it was confirmed that—the wild-type CCR5 gene and its Δccr5 variant were allelic, and segregated in a normal mendelian fashion (FIG. 8b). Interestingly, a cohort of 124 DNA samples originating from Central Africa (collected from Zaire, Burkina Fasso, Cameroun, Senegal and Benin) and Japan did not reveal a single Δccr5 mutant allele, suggesting that this allele is either absent or very rare in Asian, African black populations (Table I).

The consequences of the existence of a null allele of CCR5 in the normal Caucasian population were then considered in terms of susceptibility to infection by HIV-1. If, as it is predicted, CCR5 plays a major (not redundant) role in the entry of most primary virus strains into cells, then Δccr5/Δccr5 individuals should be particularly resistant to HIV-1 challenge, both in vitro and in vivo. The frequency of the Δccr5/Δccr5 genotype should therefore be significantly lower in HIV-1 infected patients, and increased in exposed-uninfected individuals. Also, if heterozygotes have a statistical advantage due to the lower number of functional receptors on their white blood cells, or to the possible dominant-negative properties of the mutant allele, the frequency of heterozygotes (and mutant alleles) should be decreased in HIV-infected populations. These hypotheses were tested by genotyping a large number of seropositive Caucasian individuals (n=645) belonging to cohorts originating from various hospitals from Brussels, Liège and Paris (Table I). Indeed, it was found that within this large series, the frequency of the null Δccr5 allele was significantly reduced from 0.092 to 0.053 ($p<10^{-5}$). The frequency of heterozygotes was also reduced from 0.162 to 0.106 ($p<0.001$) and not a single Δccr5/Δccr5 individual could be found ($p<0.01$).

Altogether, functional and statistical data suggest that CCR5 is indeed the major co-receptor responsible for natural infection by M-tropic HIV-1 strains. Individuals homozygous for the null Δccr5 allele (about 1% of the Caucasian population) have apparently a strong resistance to infection. It is unclear at this point whether resistance to HIV-1 is absolute or relative, and whether resistance will vary depending on the mode of viral contamination. Larger cohorts of seropositive individuals will have to be tested in order to clarify this point. Heterozygotes have a milder though significant advantage: assuming an equal probability of contact with HIV, it can be inferred from Table I that heterozygotes have a 39% reduction in their likeliness of becoming seropositive, as compared to individuals homozygous for the wild-type CCR5 allele. Both a decrease in functional CCR5 receptor number, and a dominant-negative effect of Δccr5 in vivo, comparable to what is observed in the in vitro experiments (FIG. 7) are possible explanations for this relative protection. The mutant allele, which can be regarded as a natural knock-out in human, is not accompanied by an obvious phenotype in homozygous individuals. Nevertheless, the lack of overt phenotype, taken together with the relative protection that characterizes heterozygous subjects, suggests that pharmacological agents that selectively block the ability of HIV-1 to utilize CCR5 as a cofactor, could be effective in preventing HIV-1 infection, and would be predicted not be associated with major side effects resulting from CCR5 inactivation. These pharmaceutical agents could be used with other compounds which are able to block other chemokine receptors used as co-receptors by some HIV-primary isolates in order to infect other cells [47]. The prevalence of the null allele in the Caucasian population raises the question of whether pandemia of HIV (or related viruses using the same co-receptor) have contributed during mankind's evolution to stabilize by selection the mutant ccr5 allele at such a high frequency.

Production of Antibodies Anti-CCR5

Antibodies were produced by genetic immunisation. Six week old females balb/c mice were used. DNA coding for the human CCR5 receptor was inserted in the expression vector pcdna3 under the control of the CMV promotor and 100 μg DNA was injected in the anterior tibial muscle, five days after pre-treatment of this muscle with cardiotoxine (from venom of Naja Nigricolis). Injections were repeated twice at three week intervals. Fifteen days after the last injection, blood was taken from each animal and sera were tested for the presence of anti-CCR5 antibodies.

Test of Sera Using Fluorescence Activated Cell Sorter (FACS)

Sera were tested by fluorescence activated cell sorting using recombinant CHO cells expressing the CCR5 receptor. Briefly, cells were detached using a PBS-EDTA-EGTA solution and incubated into PBS-BSA medium for 30 minutes at room temperature with 5 μl serum on the basis of 100,000 cells per tube. Cells were then washed and incubated for 30 minutes in ice together with anti-mouse antibody labelled with fluorescein. Cells were washed, taken up into 200 μl of a PBS-BSA solution and fluorescence was analysed by FACS (FACSCAN, Becton-Dickinson). 10,000 cells were counted. Wild type CHO or recombinant CHO cells expressing the human CCR2b receptor were used as controls.

When tested by FACS analysis 2 weeks after the last injection (FIG. 9), all the sera from mice immunised with CCR5 CDNA, clearly recognised the native receptor expressed on CHO cells (mean of fluorescence=200), without significant cross reaction with control cells expressing CCR2b (mean of fluorescence=20).

Sera were tested on either a CHO cell line expressing high level of CCR5 receptor (black histogram) or a CHO cell line expressing CCR2b receptor (white histogram) as negative control. Each serum was tested individually.

Antibodies Anti-CCR5 and HIV Infectivity

Peripheral blood mononuclear cells (PBMC) from one donor homozygous from wild type CCR5 gene, were isolated and cultivated 3 days in presence of PHA.

On day 4, 800 μl of cells ($10^5$ cells/ml) were incubated with 8 μl of sera from mice immunised with CCR5 CDNA, 30 minutes at 37° C. 1 ml of viral solution (JRCSF HIV strain) is then added and incubated during 2 hours. Cells were then washed twice and cultivated during 15 days.

Aliquot of medium is taken at days 0, 4, 7, 10 and 14 and the dosage of antigen p24 is performed.

Figure 10:
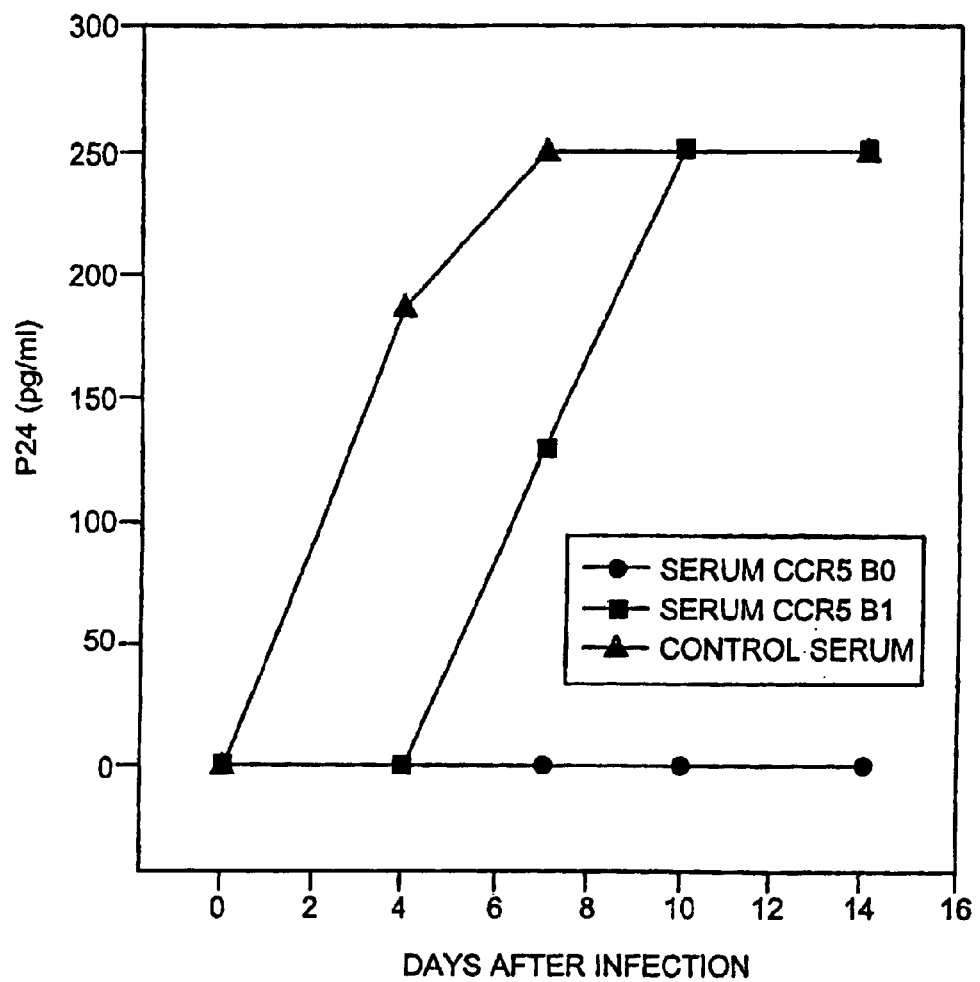
FIG. 10 represents the inhibition of HIV infectivity with anti-CCR5 antibodies.

14 days after the beginning of the experiment, one serum (serum B0) totally block the production of p24, indicating its ability to block the infection of the lymphocytes by this HIV strain (FIG. 10). Other serums also exhibit a partial or total effect on this infection (serum A2 and B1). All the other sera did not show any effect on this infection.

Production of Monoclonal Antibodies

Mice with the highest title of CCR5 antibodies were selected for monoclonal antibodies production and injected intravenously with $10^7$ recombinant CHO-K1 cells expressing human CCR5 receptors. Three days later, animals were sacrificed and fusion of splenic cells or cells from lymph nodes near the site of injection with SP2/0 myeloma cells, were performed. Fusion protocol used was that of Galfre et al. (Nature 266, 550 (1977)). A selective HAT (hypoxanthine/aminopterin/thymidin) medium is used to select hybridomas and their supernatants are tested by FACS using recombinant CHO cells expressing the human CCR5 receptor, as it was done for the sera. Positives hybridomas are then cloned by limited dilution. Clones that are shown positive by FACS analyses are then expanded and produced in ascites in balb/C mice.

TABLE 1

| | Seronegative | | | Seropositive | | | |
|---|---|---|---|---|---|---|---|
| | Number | Frequency | Standard error | Number | Frequency | Standard error | Chi-squared |
| Genotypes: | | | | | | | |
| CCR5/CCR5 | 582 | 0.827 | 0.014 | 645 | 0.892 | 0.012 | 2 degrees of |
| CCR5/Δ CCR5 | 114 | 0.162 | 0.014 | 78 | 0.108 | 0.012 | freedom |
| CCR5/Δ CCR5 | 8 | 0.011 | 0.004 | 0 | 0.000 | <0.001 | 17.7 |
| Total: | 704 | 1.000 | | 723 | 1.000 | | $p < 0.0005$ |
| Alleles: | | | | | | | |
| CCR5 | 1278 | 0.908 | 0.008 | 1368 | 0.946 | 0.006 | 1 degree of |
| Δ CCR5 | 130 | 0.092 | 0.008 | 78 | 0.054 | 0.006 | freedom |
| Total: | 1408 | 1.000 | | 1446 | 1.000 | | $p < 0.0005$ |

References

1. Ahuja et al. (1992) *Nature Genetics* 2, 31–36.
2. Alam et al. (1994) *J. Immunol.* 153, 3155–3159.
3. Alam et al. (1992) *J. Exp. Med.* 176, 781–786.
4. Baggiolini et al. (1994) *Advances in immunology*, Academic press. Ed. Dixon, F. J. 55, 97–179.
5. Birkenbach et al. (1993) *J. Virol.* 67, 2209–2220.
6. Broxmeyer et al. (1990) *Blood* 76, 1110–1116.
7. Broxmeyer et al. (1993) *J. Immunol.* 150, 3448–3458.
8. Charo et al. (1994) *Proc. Natl. Acad. Sci.* 91, 2752–2756.
9. Cocci et al. (1995) *Science* 270, 1811–1815.
10. Combadiere et al. (1995) *J. Biol. Chem.* 270, 16491–16494.
11. Desarnaud et al. (1994) *Biochem. J.* 299, 367–373.
12. Devereux et al. (1984) *Nucleic Acids Res.* 12, 387–395.
13. Dobner et al. (1992) *Eur. J. Immunol.* 22, 2795–2799.
14. Feinberg et al. (1983) *Anal. Biochem.* 132, 6–13.
15. Franci et al. (1995) *J. Immunol.* 154, 6511–6517.
16. Gao et al. (1995) *J. Biol. Chem.* 270, 17494–17501.
17. Gao et al. (1993) *J. Exp. Med.* 177, 1421–1427.
18. Gong et al. (1995) *J. Exp. Med.* 181, 631–640.
19. Hébert et al. (1993) *J. Biol. Chem.* 268, 18549–18533.
20. Holmes et al. (1991) *Science* 253, 1278–1283.
21. Jazin et al. (1993) *Regul. Peptides* 47, 247–258.
22. Kozak, M. (1989) *J. Cell. Biol.* 108, 229–241.
23. Kuna et al. (1992) *J. Immunol.* 149, 636–642.
24. Libert et al. (1989) *Science* 244, 569–572.
25. Matsuoka et al. (1993) *Biochem. Biophys. Res. Commun.* 194, 504–511.
26. Mc Master et al. (1977) *Proc. Natl Acad. Sci. USA* 74, 4835–4838.
27. McColl et al. (1993) *J. Immunol.* 150, 4550–4560.
28. Mollereau et al. (1993) *Genomics* 16, 248–251.
29. Murphy, P. M. (1994) *Annu. Rev. Immunol.* 12, 593–633.
30. Murphy et al. (1991) *Science* 253, 1280–1283.
31. Neote et al. (1993) *Cell* 72, 415–425.
32. Oppenheim et al. (1991) *Ann. Rev. Immunol.* 9, 617–648.
33. Owicki et al. (1992) *Biosensors Bioelectronics* 7, 255–272.
34. Parmentier et al. (1989) *Science* 246, 1620–1622.
35. Perret et al. (1990) *Biochem. Biophys. Res. Commun.* 17, 1044–1050.
36. Pleass et al. (1995) *Fourth International Chemokine Symposium*, Bath (UK), 27–30 June, P47.
37. Power et al. (1995) *J. Biol. Chem.* 270, 19495–19500.
38. Rot et al. (1992) *J. Exp. Med.* 176, 1489–1495.
39. Sambrook et al. (1989) *Molecular Cloning: A Laboratory Manual*, 2nd Ed., Cold Spring Harbor Laboratory, Cold Spring Harbor, N.Y.
40. Sozzani et al. (1994) *J. Immunol.* 152, 3615–3622.
41. Strader et al. (1994) *Annu. Rev. Biochem.* Ed. Dixon, R. A. F. 63, 101–132.
42. Thomas, P. S. (1980). *Proc. Natl. Acad. Sci. USA* 77, 5201–5205.
43. Vaddi et al. (1994) *The FASEB Journal* 8, A502.
44. Yamagami et al. (1994) *Biochem. Biophys. Res. Commun.* 202, 1156–1162.
45. Deng et al. (1996) *Nature* 381, 661–666.
46. Drajic et al. (1996) *Nature* 381, 667–673.
47. Doranz et al. (1996) *Cell* 85, 1149–1158.
48. Choe et al. (1996) *Cell* 85, 1135–1148.
49. Akhatib et al. (1996) *Science* 272, 1955–1958.
50. Feng et al. (1996) *Science* 272, 872–877.
51. Paxton et al. (1996) *Nat. Med.* 2, 412–417.
52. Nomura et al. (1993) *Int. Immunol.* 5, 1239–1249.
53. Loetscher et al. (1994) *J. Biol. Chem.* 269, 232–237.
54. Collman et al. (1992) *J. Virol.* 66, 7517–7521.
55. Detels et al. (1994) *J. Acquir. Immun. Defic. Sundr.* 7, 1263–1269.
56. Taylor R. J. (1994) *J. NIH Res.* 6, 29–31.
57. Wainberg et al. (1987) *Clin. Exp. Immunol.* 1987, 136–142.
58. Williams et al. (199!) *Virology* 184, 723–728.
59. Spria et al. (1995) *J. Virol.* 69, 422–429.
60. Haynes et al. (1996) *Science* 271, 324–328.
61. Ben-Baruch et al. (1995) *J. Biol. Chem.* 270, 11703–11706.
62. Nussbaum et al. (1994) *J. Virol.* 68, 5411–5422.

We claim:

1. An antibody which binds to a polypeptide comprising amino acid residues 185 to 215 of SEQ ID NO: 6.

2. An antibody which binds to a polypeptide consisting of amino acid residues SEQ ID NO:13.

3. An antibody which binds to a polypeptide encoded by a nucleic acid comprising residues 792 to 884 of SEQ ID NO: 3, wherein said polypeptide has the same reading frame as the sequence of SEQ ID NO: 6.

4. An antibody which binds to a polypeptide encoded by a nucleic acid consisting of residues 792 to 884 of SEQ ID NO: 3, wherein said pqlypeptide has the same reading frame as the sequence of SEQ ID NO: 6.

5. The antibody of claim 1, 2, 3 or 4, wherein said antibody is a monoclonal antibody.

* * * * *